US011351153B2

(12) United States Patent
McDonald et al.

(10) Patent No.: US 11,351,153 B2
(45) Date of Patent: Jun. 7, 2022

(54) ANTIMICROBIAL COMPOSITIONS CONTAINING A SYNERGISTIC COMBINATION OF ACTIVATED CREATININE AND AN IMIDAZOLE ANTIFUNGAL AGENT

(71) Applicant: Board of Regents of the University of Nebraska, Lincoln, NE (US)

(72) Inventors: Thomas McDonald, Omaha, NE (US); Steven M. Tracy, Davis, CA (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 16/474,173

(22) PCT Filed: Dec. 27, 2017

(86) PCT No.: PCT/US2017/068505
§ 371 (c)(1),
(2) Date: Jun. 27, 2019

(87) PCT Pub. No.: WO2018/125904
PCT Pub. Date: Jul. 5, 2018

(65) Prior Publication Data
US 2019/0314340 A1    Oct. 17, 2019

Related U.S. Application Data

(60) Provisional application No. 62/439,450, filed on Dec. 27, 2016.

(51) Int. Cl.
| | |
|---|---|
| *A61K 31/4166* | (2006.01) |
| *A61P 31/04* | (2006.01) |
| *A61P 31/10* | (2006.01) |
| *A61K 9/00* | (2006.01) |
| *A61K 31/4164* | (2006.01) |

(52) U.S. Cl.
CPC ........ *A61K 31/4166* (2013.01); *A61K 9/0014* (2013.01); *A61K 31/4164* (2013.01); *A61P 31/04* (2018.01); *A61P 31/10* (2018.01)

(58) Field of Classification Search
CPC .................................................. A61K 31/4166
See application file for complete search history.

(56) References Cited

U.S. PATENT DOCUMENTS

| | | | | |
|---|---|---|---|---|
| 2003/0083380 | A1* | 5/2003 | Yu ........................ | A61K 9/0014 514/557 |
| 2004/0220264 | A1* | 11/2004 | Yu ........................ | A61K 31/198 514/554 |
| 2010/0215707 | A1* | 8/2010 | McDonald .............. | A61L 26/00 424/409 |
| 2013/0243847 | A1 | 9/2013 | McDonald et al. | |

FOREIGN PATENT DOCUMENTS

WO    2013076160 A1    5/2013

OTHER PUBLICATIONS

International Search Report and Written Opinion, PCT/US2017/068505, dated May 1, 2018.

* cited by examiner

*Primary Examiner* — Svetlana M Ivanova
(74) *Attorney, Agent, or Firm* — Bradley Arant Boult Cummings LLP

(57) ABSTRACT

An antimicrobial composition containing a synergistic combination of an imidazole antifungal agent and activated creatinine is provided, wherein the imidazole antifungal agent represents in the range of about 0.5 mol % to about 30 mol % of the combination of the antifungal agent and the activated creatinine in the composition. Methods for treating bacterial infections, fungal infections, viral infections, and wounds are also provided, as are other methods of use, including methods for disinfecting inert surfaces, methods for preserving food products, and methods for treating plants. In addition, the invention provides a method for enhancing the antifungal effect of an imidazole antifungal agent as well as a method for enhancing the antibacterial effect of activated creatinine. Compositions and methods involving use of activated 2-amino-imidazol-4-one analogs other than activated creatinine are also provided.

21 Claims, 13 Drawing Sheets

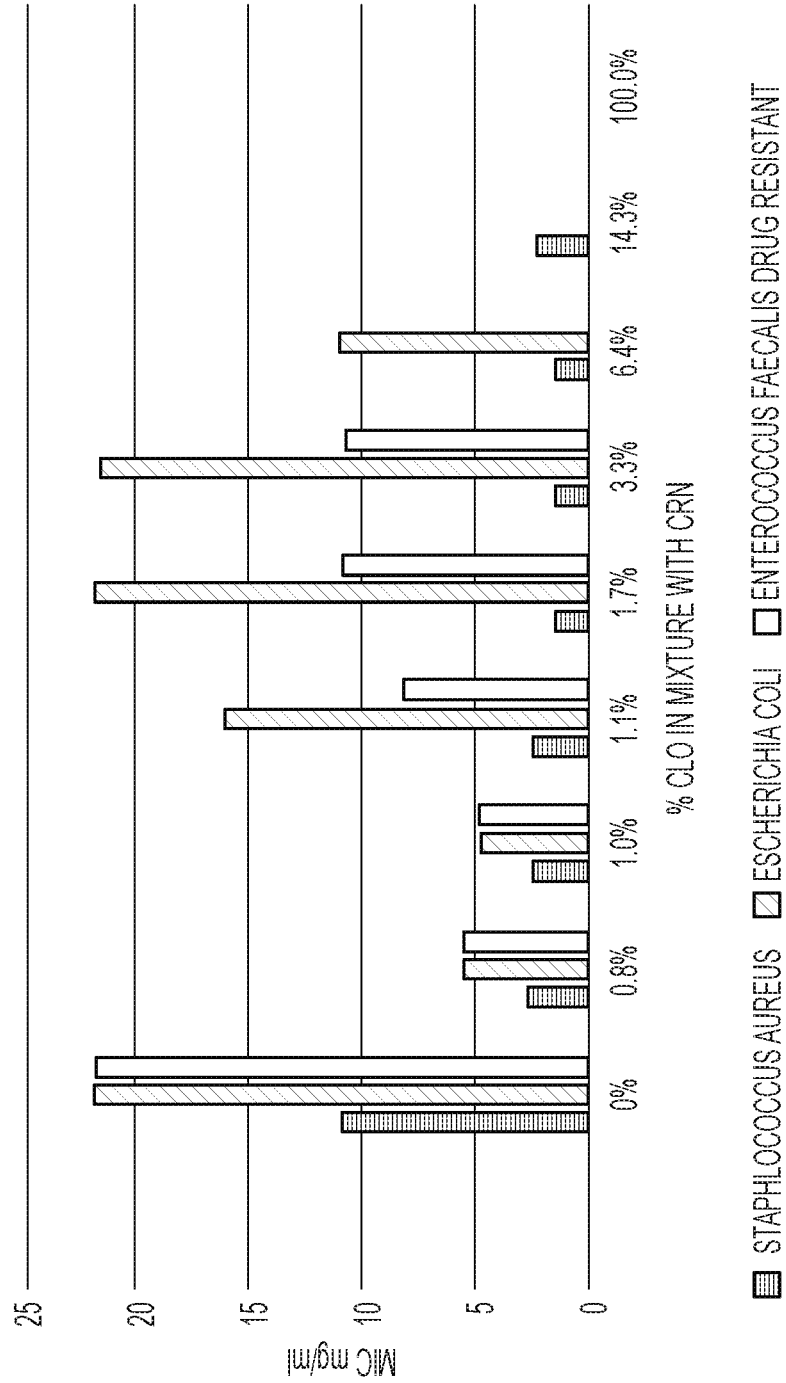

S. AUREAS

E. FAECALIS

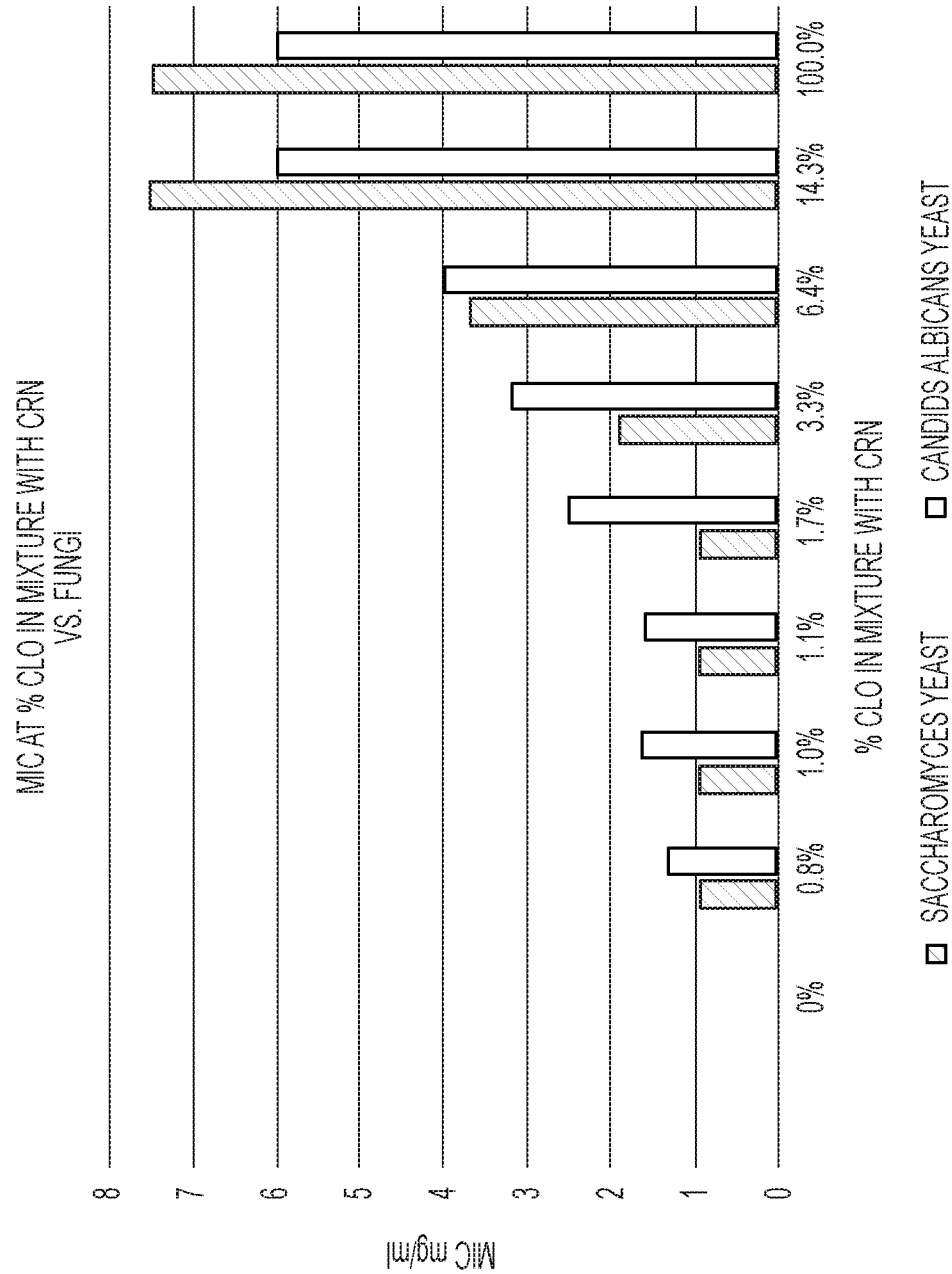

FIG. 4
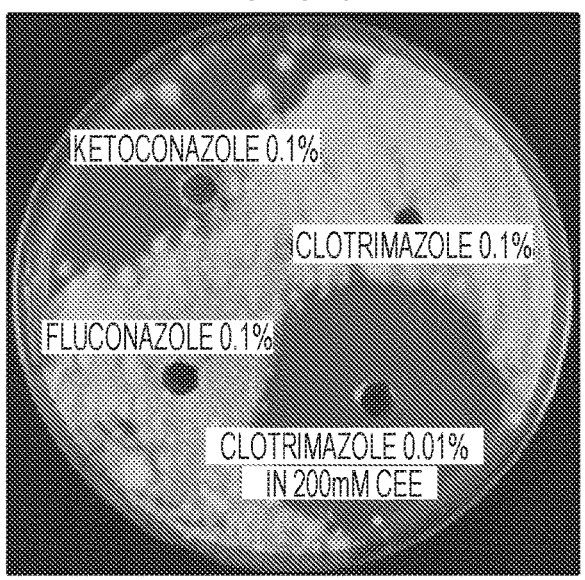
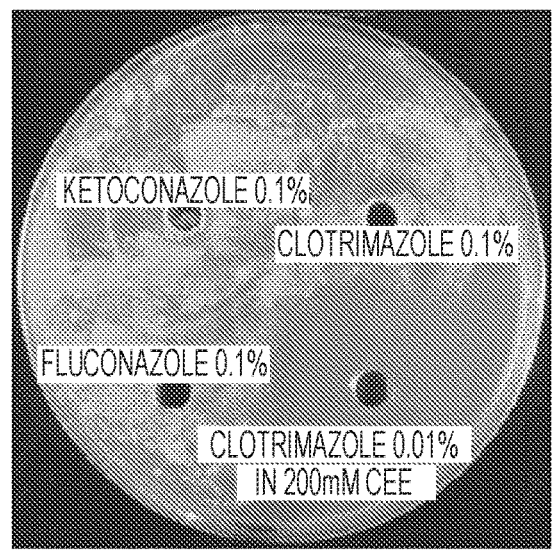

FIG. 8
SACCHAROMYCES CEREVISIAE
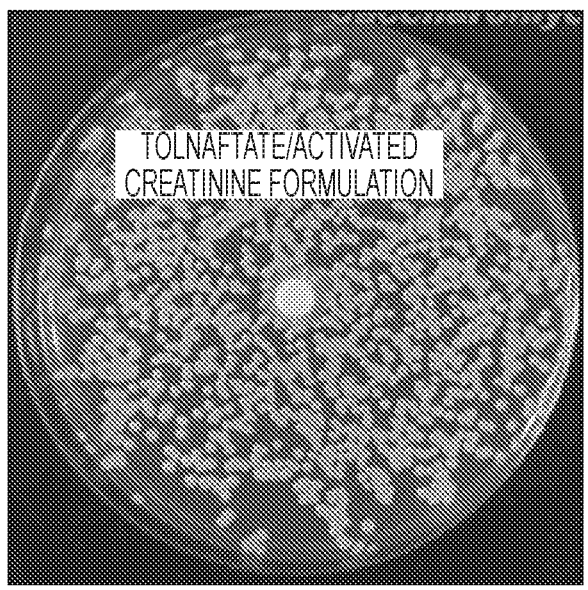 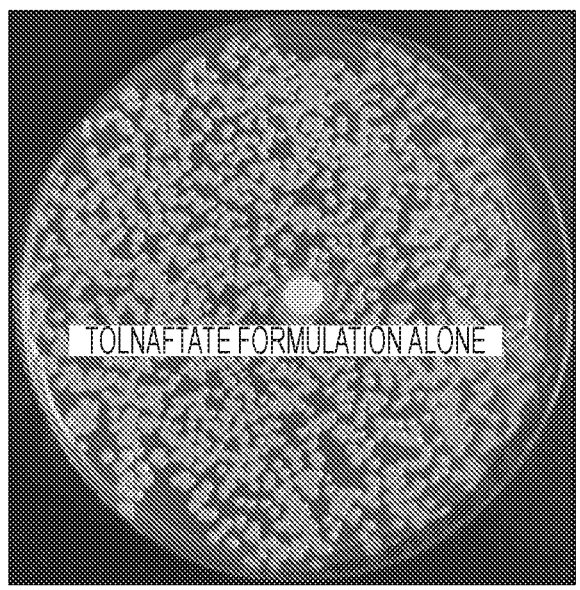
TOLNAFTATE/ACTIVATED CREATININE FORMULATION     TOLNAFTATE FORMULATION ALONE

FIG. 10
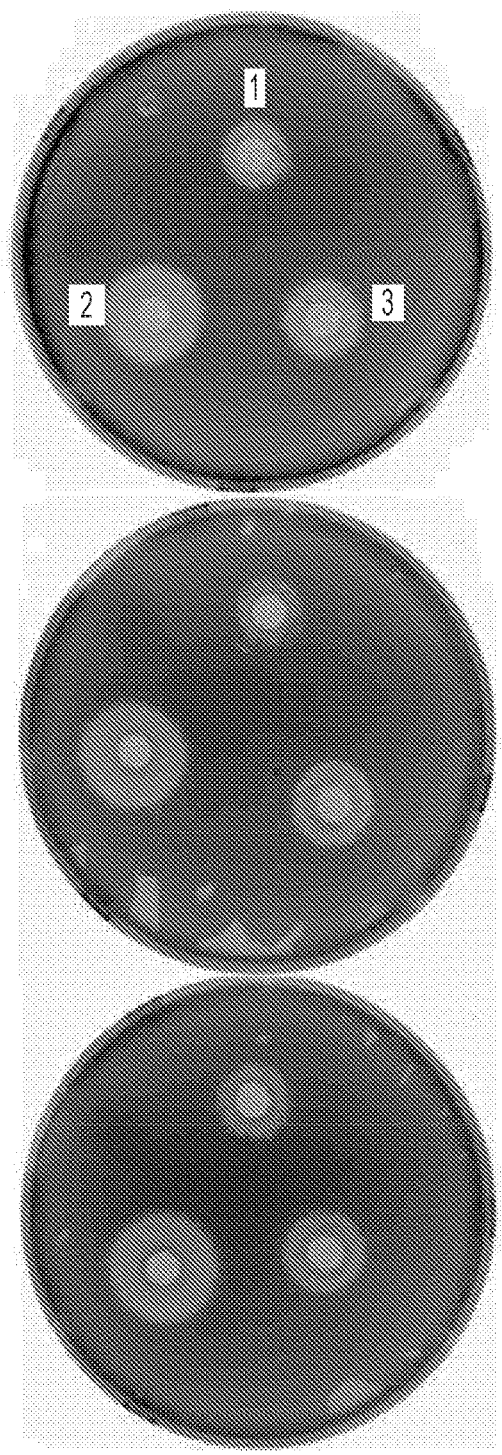
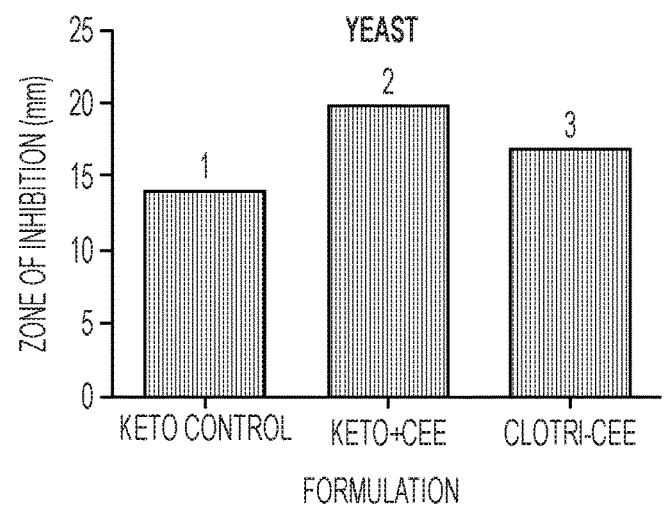
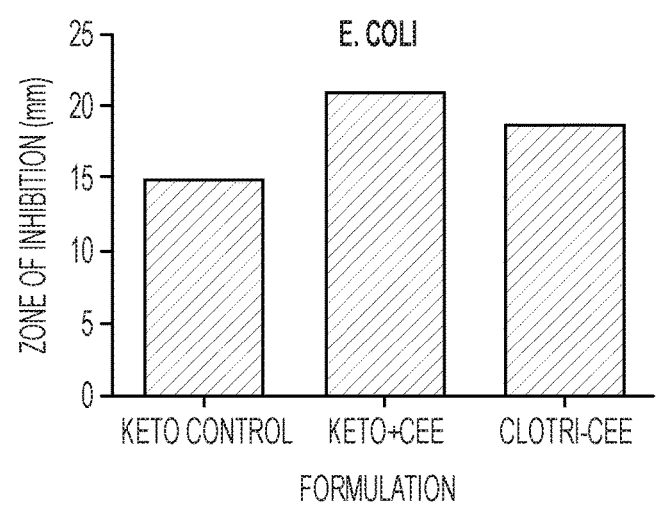
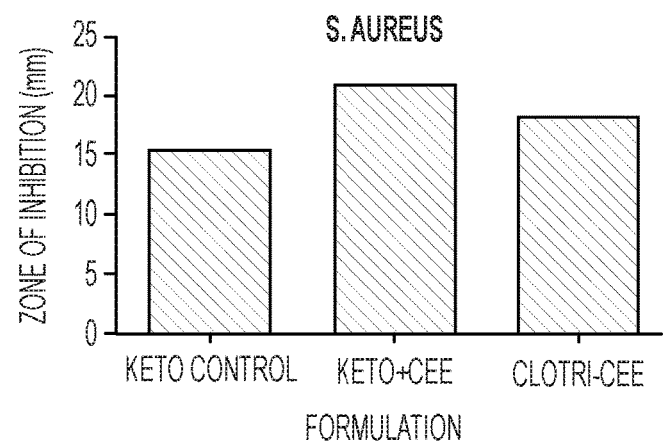

CANDIDA ALBICANS

48 HOURS AT 37 DEGREES C PSEUDOMONAS

ANTIMICROBIAL COMPOSITIONS CONTAINING A SYNERGISTIC COMBINATION OF ACTIVATED CREATININE AND AN IMIDAZOLE ANTIFUNGAL AGENT

BACKGROUND OF THE INVENTION

1. Technical Field

The present invention relates generally to antimicrobial compositions and methods of using those compositions. The invention additionally relates to antimicrobial compositions and methods for treatment of bacterial infections, fungal infections, and wounds, as well as to methods of disinfection in other contexts. Invention has utility in numerous fields, including medicine, pharmaceuticals, and drug delivery, as well as in agriculture, animal health and production, material preservation, sanitation, and other fields of use in which an antimicrobial activity is required or beneficial.

2. Description of Related Art

There is an ongoing need for antimicrobial agents and formulations that exhibit greater efficacy and lower potential toxicity than the antimicrobial products currently in use. For example, there is a continuing and critically important need for pharmaceutical formulations that are effective in preventing and treating infections, particularly bacterial and fungal infections. Many of the current antimicrobial products intended for topical application suffer from multiple drawbacks. Topical antimicrobial formulations, for instance, can be somewhat less than ideally effective, particularly against stubborn or recurring infections. They may also contain one or more additives that cause the user to feel discomfort, as a result of irritating or sensitizing the skin. Furthermore, they may lead to the development of drug resistance within the microbial population. Along the same lines, a fairly high concentration of active agent may be necessary to achieve the intended therapeutic effect, and the high concentration can, in turn, cause the user discomfort and/or result in an undesirable skin reaction. Furthermore, topical antimicrobial formulations are typically effective against only a single type of infection, i.e., a fungal infection or a bacterial infection, but not both.

Currently, there is an urgent need in medicine and other fields for antimicrobial formulations that will kill fungi and bacteria that are becoming or have become resistant to current antimicrobial agents. Antimicrobial resistance (AMR) has been defined by the World Health Organization as the ability of a microorganism (such as bacteria, viruses, and some parasites) to stop an antimicrobial (such as antibiotics, antivirals or antimalarials) from working against it. As a result, standard treatments become ineffective, infections persist and may spread to others. AMR is not only problematic in the health care context, but is also a significant concern in the fields of agriculture, animal food product, and numerous other industries. Problems with antimicrobial resistance have become increasingly urgent, and extensive efforts by researchers in the field have failed to provide solutions.

An ideal antimicrobial composition, including, but not limited to, antimicrobial compositions for topical application, would overcome each of the aforementioned limitations.

A compound of interest as a potential antibacterial agent is "antibacterially activated creatinine" or simply "activated creatinine," described in U.S. Patent Publication No. 2013/0243847 A1 to McDonald et al., incorporated herein by reference. As explained in that patent application, creatinine (2-amino-1-methyl-4-imidazolidinone) can be activated to a form that has antibacterial activity by admixture of creatinine with a suitable acid to form an acid addition salt. The '847 publication also explains that creatinine is a stable, natural end product of creatine catabolism in muscle tissue, and is present in serum and in urine at approximately 100 $\mu$M concentrations. As such, activated creatinine is a naturally occurring product and safe for use as a topical pharmaceutical agent even at relatively high concentrations. Finally, it should be noted that activated creatinine, as discussed in the '847 publication, was found to have antibacterial activity against both gram negative and gram positive bacteria, and against both aerobic and anaerobic bacteria.

The present invention similarly makes use of activated creatinine but represents a significant improvement over the proposed antibacterial formulations of the '847 patent, as will be discussed in detail herein.

SUMMARY OF THE INVENTION

Accordingly, the invention is directed to the aforementioned need in the art, and provides an antimicrobial active agent combination useful in treating bacterial, fungal, and/or viral infections. Compositions containing the antimicrobial active agent combination can be used as antibacterial compositions, antifungal compositions, antiviral compositions, and disinfectant compositions.

In a first aspect, the invention provides an antimicrobial active agent combination and a method for treating bacterial infections and/or fungal infections, wherein the infections can include stubborn, persistent, and recurring infections. It is important to note that with the compositions and method of the invention, there is little or no likelihood that the fungal and/or bacterial organisms will develop resistance. Patients are very unlikely to experience discomfort, and high active agent concentrations are safe but unnecessary. The reason for this is the synergistic interaction that has now been discovered between the two types of active agents in the active agent combination, provided that the relative amounts of the two active agents are in a specified ratio range, as will be discussed in detail herein. The two agents are an imidazole antifungal agent and activated creatinine or another activated 2-amino-imidazol-4-one. The active agent combination is multi-purpose insofar as it can prevent, inhibit, or eliminate the occurrence or spread of bacterial and/or fungal infections, including, without limitation, bacterial and/or fungal infections in humans, animals, and plants. The invention is also useful in nontherapeutic contexts in which antimicrobial utility is required or at least advantageous, such as in hospital sanitation, plant health, agricultural production, and other areas in which an antiseptic or disinfectant composition is required or advantageous.

The antimicrobial active agent combination of an imidazole antifungal agent and activated creatinine can be incorporated into a single composition, wherein the imidazole antifungal agent represents in the range of about 0.5 mol % to about 30 mol % of the combination of the antifungal agent and the activated creatinine. As will be established infra, bidirectional synergy is generally seen within the aforementioned range. That is, the combination of the two active agents gives rise to antifungal activity that is higher than that of the imidazole antifungal agent alone, and also increases antibacterial activity beyond that seen with activated creatinine alone. The synergistic increase in antimicrobial activity is surprisingly large and clinically important. Furthermore, in addition to enhancing the effectiveness of each component, the combination of an imidazole antifungal agent and activated creatinine can actually create efficacy where none was apparent before.

In another aspect of the invention, an antimicrobial composition is provided as above wherein the composition contains at least one additional pharmacologically active agent, which may be an additional antifungal agent, an additional antibacterial agent, an additional antiviral agent, or another type of agent, such as an anti-inflammatory agent, a wound-healing agent, an anti-pruritic agent, or the like.

In another aspect of the invention, an antimicrobial composition is provided as above wherein the composition contains a pharmaceutically acceptable topical carrier and the antimicrobial composition is adapted for application to a body surface.

In a further aspect of the invention, an antimicrobial composition is provided as above wherein the composition contains a pharmaceutically acceptable carrier suitable for incorporation into a systemically administrable formulation.

In still a further aspect of the invention, an antimicrobial composition is provided that comprises a combination of an imidazole antifungal agent and an activated 2-amino-imidazol-4-one analog represented by the resonance structures of formula (I)

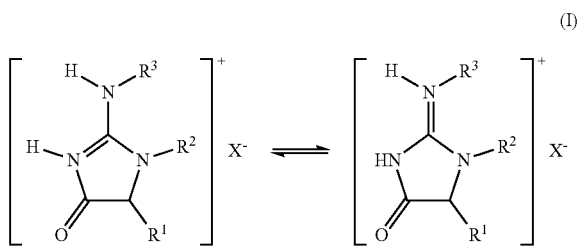

wherein:
$R^1$ is selected from hydrogen, halo, hydroxyl, sulfhydryl, $C_1$-$C_6$ alkyl, $C_1$-$C_6$ alkoxy, mono-($C_1$-$C_6$ alkyl)-substituted amino, and di-($C_1$-$C_6$ alkyl)-substituted amino;
$R^2$ is $C_1$-$C_6$ alkyl;
$R^3$ is selected from hydrogen and $C_1$-$C_6$ alkyl; and
X is a negatively charged counterion,
wherein either $R^2$ is other than methyl or at least one of $R^1$ and $R^3$ is other than H,
and further wherein the imidazole antifungal agent represents in the range of about 0.5 mol % to about 30 mol % of the combination of the antifungal agent and the activated 2-amino-imidazol-4-one analog.

Another aspect of the invention pertains to a method for treating a bacterial infection in a subject by administering to the subject an antibacterially effective amount of a pharmaceutical formulation that comprises a combination of an imidazole antifungal agent and activated creatinine, wherein the imidazole antifungal agent represents in the range of about 0.5 mol % to about 30 mol % of the combination of the antifungal agent and the activated creatinine.

In still a further aspect, an antibacterial method is provided as above wherein the bacterial infection is antibiotic-resistant.

A further aspect of the invention provides a method for treating a bacterial infection in a subject by administering to the subject an antibacterially effective amount of a pharmaceutical composition that comprises a combination of an imidazole antifungal agent and an activated 2-amino-imidazol-4-one analog represented by the resonance structures of formula (I)

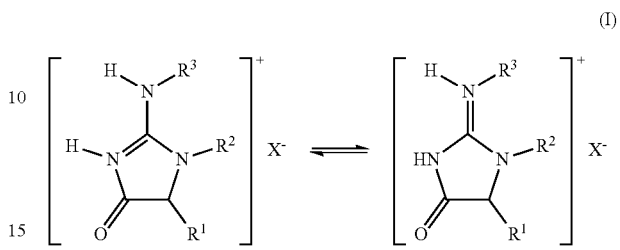

wherein $R^1$, $R^2$, $R^3$, and X are as defined previously, and further wherein the imidazole antifungal agent represents in the range of about 0.5 mol % to about 30 mol % of the combination of the antifungal agent and the activated 2-amino-imidazol-4-one analog.

Another aspect of the invention pertains to a method for treating a fungal infection in a subject by administering to the subject an effective antifungal amount of a pharmaceutical formulation that comprises a combination of an imidazole antifungal agent and activated creatinine, wherein the imidazole antifungal agent represents in the range of about 0.5 mol % to about 30 mol % of the combination of the antifungal agent and the activated creatinine.

Still a further aspect of the invention provides an antifungal method as above wherein the fungal infection is antifungal resistant.

In a further aspect of the invention, a method is provided for treating a fungal infection in a subject by administering to the subject an effective antifungal amount of a pharmaceutical composition that comprises a combination of an imidazole antifungal agent and an activated 2-amino-imidazol-4-one analog represented by the resonance structures of formula (I)

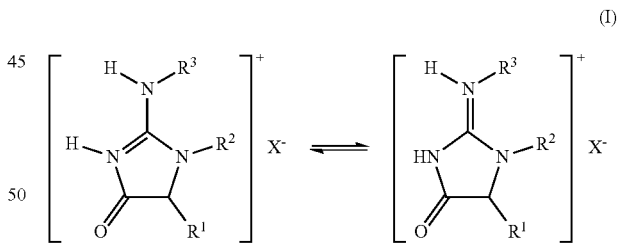

wherein $R^1$, $R^2$, $R^3$, and X are as defined previously, and further wherein the imidazole antifungal agent represents in the range of about 0.5 mol % to about 30 mol % of the combination of the antifungal agent and the activated 2-amino-imidazol-4-one analog.

An additional aspect of the invention provides a method for treating an individual suffering from both a bacterial infection and a fungal infection, by administering to the individual an effective amount of an antimicrobial pharmaceutical formulation containing a combination of an imidazole antifungal agent and activated creatinine, wherein the imidazole antifungal agent represents in the range of about 0.5 mol % to about 30 mol % of the combination of the antifungal agent and the activated creatinine.

A related aspect of the invention provides such a method wherein the individual has been undergoing treatment with antibiotics and the composition of the invention prevents or treats a fungal infection that may be incurred as a result.

Another aspect of the invention provides a method for treating an individual with both a bacterial infection and a fungal infection, by administering to the individual an effective amount of an antimicrobial composition containing a combination of an imidazole antifungal agent and an activated 2-amino-imidazol-4-one analog represented by the resonance structures of formula (I)

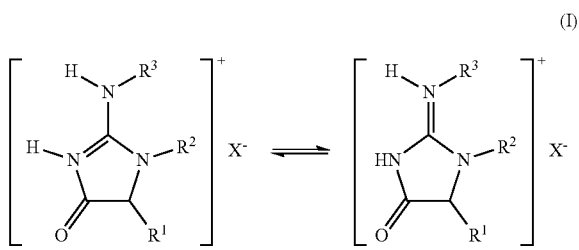

wherein $R^1$, $R^2$, $R^3$, and X are as defined previously, and further wherein the imidazole antifungal agent represents in the range of about 0.5 mol % to about 30 mol % of the combination of the antifungal agent and the activated 2-amino-imidazol-4-one analog.

Another aspect of the invention pertains to a method for treating a viral infection in a subject by administering to the subject an antibacterially effective amount of a pharmaceutical formulation that comprises a combination of an imidazole antifungal agent and activated creatinine, wherein the imidazole antifungal agent represents in the range of about 0.5 mol % to about 30 mol % of the combination of the antifungal agent and the activated creatinine. In a related aspect, the method for treating a viral infection in a subject comprises administering to the subject an effective amount of an antiviral composition containing a combination of an imidazole antifungal agent and an activated 2-amino-imidazol-4-one analog represented by the resonance structures of formula (I).

The invention also provides, in another aspect, a method for treating a wound, by administering to the wound an effective antimicrobial amount of a pharmaceutical formulation that comprises a combination of an imidazole antifungal agent and activated creatinine, wherein the imidazole antifungal agent represents in the range of about 0.5 mol % to about 30 mol % of the combination of the antifungal agent and the activated creatinine. The composition may or may not be incorporated into a wound dressing applied directly to the wound.

An additional aspect of the invention provides a method for treating inflammation, such as inflammation associated with a bacterial, fungal, or viral infection, the method involving administering to a patient in need of such treatment a composition containing activated creatinine and an imidazole antifungal agent where the antifungal agent represents about 0.5 mol % to about 30 mol % of the combination of the two agents.

Another aspect of the invention pertains to a method for increasing the antibacterial efficacy of activated creatinine, wherein the method involves combining the activated creatinine with an imidazole antifungal agent in a composition in which the imidazole antifungal agent represents in the range of about 0.5 mol % to about 30 mol % of the combination of the antifungal agent and the activated creatinine, such that the antibacterial efficacy of the composition is greater than the antibacterial efficacy of activated creatinine alone.

Another aspect of the invention pertains to a method for increasing the antifungal efficacy of an imidazole antifungal agent, wherein the method comprises combining the imidazole antifungal agent with activated creatinine in a composition in which the imidazole antifungal agent represents in the range of about 0.5 mol % to about 30 mol % of the combination of the antifungal agent and the activated creatinine, such that the antifungal efficacy of the composition is greater than the antifungal efficacy of the imidazole antifungal agent alone.

In another aspect, the invention provides a method for disinfecting an inert surface by applying to the surface an effective disinfecting amount of a composition comprising a combination of an imidazole antifungal agent and activated creatinine, wherein the imidazole antifungal agent represents in the range of about 0.5 mol % to about 30 mol % of the combination of the antifungal agent and the activated creatinine.

Many aspects of the invention are indeed surprising and unexpected: that adding a small amount of an imidazole antifungal agent to activated creatinine creates a significantly stronger antibacterial effect than that seen with activated creatinine alone; that adding a small amount of an imidazole antifungal agent to activated creatinine creates a significantly stronger antifungal effect than that seen with the imidazole antifungal agent alone; that this synergy is triggered by a relatively small percentage of the imidazole antifungal agent in the combination; that this synergy should decrease with a higher proportion of the imidazole antifungal agent in the combination; and that the antimicrobial active agent combination should deliver increased antibacterial and antifungal effects simultaneously.

Additional objects, advantages and novel features of the invention will be set forth in part in the description which follows, and in part will become apparent to those skilled in the art upon examination of the following, or may be learned by practice of the invention.

BRIEF DESCRIPTION OF THE DRAWINGS

FIG. 1 is a bar graph illustrating the variation in minimum inhibitory concentration ("MIC") of clotrimazole/activated creatinine compositions tested for antibacterial activity against *Streptococcus aureas, E. coli*, and a multiple drug-resistant strain of *Enterococcus faecalis*, as described in Example 2; the MIC is plotted as a function of the percent, by mole, of clotrimazole in a clotrimazole/activated creatinine mixture.

FIG. 3 is a bar graph illustrating the variation in MIC of clotrimazole/activated creatinine compositions tested for antifungal activity against *Saccharomyces* yeast and *Candida albicans*, as described in Example 3; the MIC is plotted as a function of the percent, by mole, of clotrimazole in a clotrimazole/activated creatinine mixture.

FIG. 4 is a photograph illustrating the comparative antifungal effects of a clotrimazole/activated creatinine composition versus 0.1% (w/v) solutions of ketoconazole, clotrimazole, and fluconazole, evaluated as described in Example 4. The lefthand side of FIG. 4 shows the results with *Penicillium* spp. 1 while on the right the results with *Penicillium* spp. 2 are shown. (Note that in the figure, the clotrimazole/activated creatinine composition is indicated as Clotrimazole 0.01% in 200 mM CEE; CEE refers to creatinine ethyl ester hydrochloride, which converts to creatinine hydrochloride in aqueous media).

FIG. 5A is a photograph showing the results obtained with the clotrimazole-only formulation, and FIG. 5B is a photograph showing the results obtained with the clotrimazole/activated creatinine composition.

FIG. 7A is a photograph showing the results obtained with the clotrimazole-only formulation, and FIG. 7B is a photograph showing the results obtained with the clotrimazole/activated creatinine composition.

FIG. 8 is a photograph illustrating the antifungal efficacy of a Tinactin® (tolnaftate)/activated creatinine composition against *Saccharomyces* spp., as described in Example 8.

FIG. 10 illustrates the comparable antifungal and antibacterial effects of a ketoconazole/activated creatinine composition versus a ketoconazole-only composition, evaluated against yeast, *E. coli*, and *S. aureas* as described in Example 10. These results also illustrate that the effectiveness of the imidazole/activated creatinine composition can vary according to the type of imidazole antifungal agent utilized in the combination.

DETAILED DESCRIPTION OF THE INVENTION

I. Definitions and Nomenclature

Figure 2A:
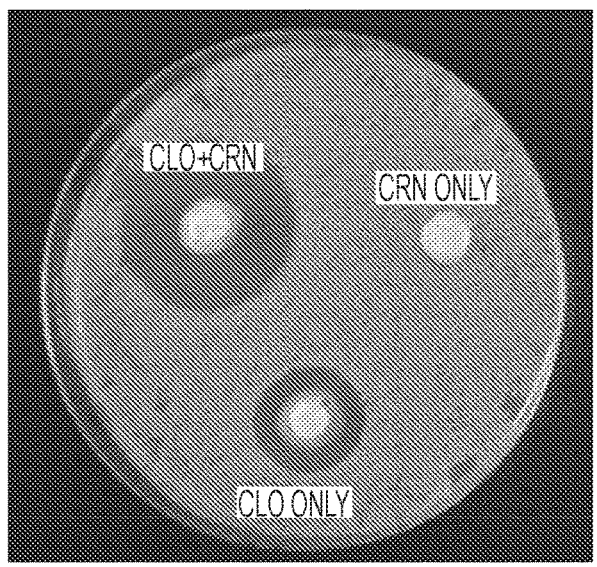
FIG. 2 is a photograph illustrating the comparative antibacterial effects of a clotrimazole/activated creatinine composition versus clotrimazole-only and activated creatinine-only formulations, evaluated as described in Example 2 (results obtained for *Staphylococcus aureas* and *Enterococcus faecalis* are provided on the left and right portions of the figure, respectively).

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "an imidazole antifungal agent" refers not only to a single such agent but also to a combination of two or more different imidazole antifungal agents, and "a pharmaceutically acceptable carrier" refers to a combination of pharmaceutically acceptable carriers, as will often be the case, as well as to a single pharmaceutically acceptable carrier, and the like.

When referring to an active agent, whether specified as a particular compound (e.g., clotrimazole) or a compound class (e.g., an imidazole antifungal agent), the term used to refer to the agent is intended to encompass not only the specified molecular entity but also its pharmaceutically acceptable, pharmacologically active analogs and derivatives, including, but not limited to, salts, esters, amides, prodrugs, conjugates, active metabolites, hydrates, crystalline forms, enantiomers, stereoisomers, and other such derivatives, analogs, and related compounds.

For instance, an imidazole antifungal agent may be modified by conversion to an ionized form such as an acid addition salt; by functionalization (e.g., via esterification or some other chemical reaction); by incorporation of one or more substituents at a ring carbon atom or a ring nitrogen atom within the imidazole moiety and/or other heterocyclic moiety within the molecular structure; by incorporation of one or more non-hydrogen substituents elsewhere in the molecular structure, e.g., to replace a C—H or N—H with C—R or N—R, respectively, where R is the non-hydrogen substituent; by incorporation of one or more additional heteroatoms in an imidazole ring, e.g., sulfur, oxygen, or an additional nitrogen atom (the latter generating a triazole); or by replacement of one of the ring nitrogen atoms in the imidazole ring with a different heteroatom, e.g., sulfur, as is the case with 1,3-thiazole. While these modifications technically generate an azole other than an imidazole per se, e.g., a triazole, thiazole, or the like, any of the aforementioned modified compounds that function at least as well as the imidazole antifungal agents expressly disclosed herein, in terms of antimicrobial activity and synergy, are intended to be encompassed within the term "imidazole antifungal agent" throughout this specification and claims.

As another example, "activated creatinine" includes prodrugs of activated creatinine and other precursors to activated creatinine, and also includes salts, esters, amides, conjugates, and the like, as well as the activated creatinine analogs embodied in formula (I), infra. The active agents or the aforementioned analogs and derivatives may be naturally occurring compounds, synthetically modified naturally occurring compounds, or chemically synthesized.

The terms "treating" and "treatment" as used herein refer to the administration of a pharmaceutical agent or composition to a subject to provide a desired pharmacological or physiological effect, and thus encompasses administration for therapeutic and/or prophylactic purposes. Treating a condition in a subject already suffering from that condition generally involves a reduction in the severity, number, and/or frequency of symptoms, the elimination of symptoms and/or underlying cause, and the improvement or remediation of damage. In the prophylactic context, treatment refers to the administration of a pharmaceutical agent or composition to a subject who is not yet suffering from a particular condition, but has been identified as at susceptible to, i.e., at risk for developing, the particular condition, where the prophylactic effect involves partially or completely preventing a condition or symptom thereof. For instance, an individual undergoing treatment with an antibiotic for a bacterial infection may have, as a result of the antibiotic, increased susceptibility to a fungal infection, and prophylactic administration of an antimicrobial composition of the invention would reduce the likelihood that the individual will contract a fungal infection.

"Treating a bacterial infection" thus encompasses preventing the bacterial infection from occurring in a subject who is susceptible to developing the infection, inhibiting the progress of the infection in a subject, and causing regression or amelioration of the infection, wherein a "bacterial infection" refers to the invasion of a host by pathogenic bacteria or excessive growth of bacteria that are normally present within the body, and the bacteria are damaging to the host body.

Analogously, "treating a fungal infection" is to be interpreted in the same manner, where a "fungal infection" refers to the invasion of a host by pathogenic fungi or excessive growth of fungi that are normally present within the body, wherein presence of the fungi is damaging to the host body.

The terms "effective amount" and "therapeutically effective amount" of a compound, active agent combination, or composition refer to an amount that is nontoxic and effective for producing a desired result, e.g., treatment of a bacterial infection or treatment of a fungal infection. The exact amount required will vary from subject to subject, depending on factors such as the age, weight and general condition of the subject, the particular infection being treated, the severity of the infection, the judgment of the clinician, the particular active agent combination used, the target microbe, and the like. The "effective amount" may be an amount that is useful when administration is carried out once or on an as-needed basis, or within the context of an ongoing dosage regimen.

By "pharmaceutically acceptable" is meant a material that is not biologically or otherwise undesirable, i.e., the material may be incorporated into a pharmaceutical composition as provided herein and not cause any substantial undesirable biological effects or interact in a deleterious manner with any of the other components of the composition. When the term "pharmaceutically acceptable" is used to refer to a pharmaceutical carrier or excipient, it is implied that the carrier or excipient has met the required standards of toxicological and manufacturing testing and/or that it is included on the Inactive Ingredient Guide prepared by the U.S. Food and Drug administration.

A "pharmacologically active analog" refers to a structural analog having the same type of pharmacological activity as the parent compound and approximately equivalent in degree.

As used herein, "subject" or "individual" or "patient" refers to any subject for whom or which therapy is desired, and generally refers to the recipient of the therapy to be practiced according to the invention. The subject can be any living organism, plant or animal. If animal, the subject will typically be a vertebrate, usually a mammal, and for most purposes will be human.

The term "topical administration" is used in its conventional sense to mean delivery of a topical drug or pharmacologically active agent to the skin or other body surface, as in, for example, the treatment of various skin infections. The term "transdermal administration" is also used in the conventional sense to refer to the delivery of a systemically active pharmacologically active agent through a body surface, which may be either skin or mucosal tissue. Topical administration provides a local rather than a systemic effect, while transdermally administered agents enter the bloodstream and are systemically active.

As used herein an "antifungal" agent refers to a compound or composition that is fungistatic or fungicidal.

The term "combination" of an imidazole antifungal agent and activated creatinine may refer to a mixture or blend of the two active agents, as may be present in a pharmaceutical formulation, and to a combination that does not involve mixture. The term "combination" when used in the context of a method of use encompasses not only simultaneous administration of the two active agents, which may or may not be present in a single composition, but also separate, i.e., sequential administration of the two active agents. In the pharmaceutical context, this means that the imidazole antifungal agent and the activated creatinine may be administered to a subject in a single formulation or in two different formulations. In the latter case, the two different formulations, e.g., an imidazole antifungal agent dosage form and an activated creatinine dosage form, may be simultaneously or sequentially administered.

As used herein, the phrase "having the formula" or "having the structure" is not intended to be limiting and is used in the same way that the term "comprising" is commonly used.

In the chemical structures herein, the term "alkyl" as used herein refers to a branched or unbranched saturated hydrocarbon group typically although not necessarily containing 1 to about 6 carbon atoms, such as methyl, ethyl, n-propyl, isopropyl, n-butyl, isobutyl, t-butyl, n-pentyl, and the like, as well as cycloalkyl groups such as cyclopentyl and cyclohexyl. Preferred alkyl substituents contain 1 to 3 carbon atoms, and particularly preferred such substituents contain 1 or 2 carbon atoms (i.e., methyl and ethyl). If not otherwise indicated, the term "alkyl" includes linear, branched, cyclic, unsubstituted, substituted, and/or heteroatom-containing alkyl.

The term "alkoxy" as used herein intends an alkyl group bound through a single, terminal ether linkage; that is, an "alkoxy" group may be represented as —O-alkyl where "alkyl" is as defined above.

"Optional" or "optionally" means that the subsequently described circumstance may or may not occur, so that the description includes instances where the circumstance occurs and instances where it does not.

II. The Active Agent Combination

The compositions and methods of the invention make use of a combination of active agents: an imidazole antifungal agent; and activated creatinine. The relative amounts of the two agents in the combination are selected to provide synergy. The synergy is generally although not necessarily bidirectional, meaning that the activated creatinine significantly increases the antifungal activity of the imidazole antifungal agent and the imidazole antifungal agent significantly increases the antibacterial activity of the activated creatinine. In some cases, i.e., with some active agents and agent combinations, a type of synergy is provided in which one of the active agents imparts efficacy to the other active agent that is otherwise ineffective in the particular method, e.g., functionality in the treatment of a particular bacterial infection or treatment of a particular fungal infection. For instance, while a formulation containing only clotrimazole as the active agent does not exhibit antifungal activity versus penicillium yeast, combining the clotrimazole with activated creatinine generates antifungal activity against both *Penicillium* spp. and *Penicillium* spp. 2 (see Example 4 and FIG. 4). Similarly, while activated creatinine by itself is ineffective in treating *S. aureas*, as is clotrimazole, the combination of the two provides a composition that does exhibit antibacterial efficacy against the organism (see Example 2 and FIG. 2).

The antimicrobial compositions of the invention are thus a synergistic active agent combination. To achieve synergy, regardless of end use, i.e., antibacterial utility, antifungal utility or disinfectant activity, the relative amounts of each active agent in the combination should be such that the imidazole antifungal agent represents in the range of about 0.5 mol % to about 30 mol % of the combination of the antifungal agent and the activated creatinine. This is equivalent to an antifungal agent/activated creatinine mole ratio of about 1:199 to about 1:2.33 Preferably, the imidazole antifungal agent represents in the range of 0.5 mol % to about 20 mol % of the combination of the antifungal agent and the activated creatinine, equivalent to an antifungal agent/activated creatinine mole ratio of about 1:199 to about 1:4. Within these ranges, the relative amounts of the two active agents necessary to achieve a synergistic effect vary, to some extent, by microbe, and also, to some extent, by the imidazole antifungal agent selected. However, the optimal ratio for any particular microbe can be determined using methods known in the art and/or described in the pertinent literature, e.g., methods for evaluating antibacterial efficacy and/or antifungal efficacy. For gram-positive bacteria such as *Staphylococcus* infections, the imidazole antifungal agent should represent about 0.5 mol % to about 15 mol % of the antifungal agent/activated creatinine combination, while for gram-negative bacteria such as *E. coli*, the imidazole antifungal agent should represent about 0.5 mol % to about 6.5 mol % of the antifungal agent/activated creatinine combination. The ranges for treating specific types of fungal infections, while also generally about 0.5 mol % to about 30 mol %, may vary with the fungal infection as well as by fungal infection type, e.g., yeast or mold infections. The mole ratio ranges noted above are generally those that give rise to maximum synergy. However, there may be ratios outside these ranges where synergy also occurs. It should be noted that a smaller increase in antimicrobial effectiveness may still represent a medically significant improvement, even though it is not the multi-fold improvement available at the optimal ratios. Accordingly, it is not the applicant's intention in specifying the above ratios to exclude from this invention other ratios at which the discovered synergy may yield an increase in antimicrobial efficacy.

The imidazole antifungal agent can be any compound now known or which has yet to be discovered which contains an imidazole ring or a modified imidazole ring, and that acts as an antifungal agent by itself or is rendered antifungal by combining it with activated creatinine.

Imidazole antifungal agents useful in conjunction with the present invention include, without limitation, bifonazole, butoconazole, chlormidazole, clotrimazole, croconazole, econazole, elubiol, fenticonazole, flutrimazole, isoconazole, ketoconazole, luliconazole, miconazole, neticonazole, omoconazole, oxiconazole, sertaconazole, sulconazole, and tiaconazole. Generally preferred imidazole antifungal agents in the context of the present invention include clotrimazole, ketoconazole, and miconazole, for local, e.g., topical administration, and, for systemic use, i.e., for delivery to the circulatory system via the oral, parenteral, transdermal, or other routes, ketoconazole is typically preferred.

As alluded to Section I, above, an imidazole antifungal agent may be modified by incorporation of one or more substituents at a carbon atom or nitrogen atom within the molecular structure; by functionalization (e.g., via esterification or some other chemical reaction); or by incorporation of one or more additional heteroatoms in an imidazole ring, e.g., sulfur, oxygen, or an additional nitrogen atom. Such compounds are encompassed within the term "imidazole antifungal agent" herein, and include, by way of example rather than limitation, other azole antifungal agents such as abafungin, a thiazole, and the triazole antifungal agents albaconazole, efinaconazole, epoxiconazole, fluconazole, fosfluconazole, hexaconazole, isavuconazole, itraconazole, posaconazole, propiconazole, ravuconazole, terconazole, and voriconazole.

The term "activated creatinine" refers to a form of creatinine that exhibits antimicrobial activity. Antimicrobially activated creatinine refers to a protonated form of creatinine (or a precursor thereof, as will be explained infra), generally referred to as the creatininium cation or as simply "creatininium," wherein in nonaqueous form it will generally be associated with a negatively charged counterion as an acid addition salt.

Creatinine can be represented by the resonance structures of formula (1a) and (1b):

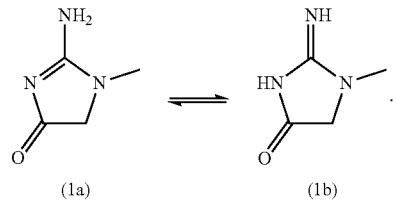

It is to be understood, of course, that the two resonance structures shown are not discrete chemical entities, and differ from each other only with respect to the placement or localization of bonding and nonbonding electrons.

As explained in U.S. Patent Publication No. 2013/0243847 A1 to McDonald et al., cited earlier herein, activation of creatinine can involve converting the electronically neutral creatinine molecule to the protonated form, or it can involve conversion of a protonated precursor of creatinine to protonated creatinine. Other methods of generating protonated creatinine can also be used.

Admixture of creatinine with an acid, or addition of creatinine to an aqueous medium having a pH below about 6.5, preferably in the range of about 5.0 to about 5.5, results in the protonated form. Protonated creatinine is represented by the resonance structures of formula (2a) and (2b)

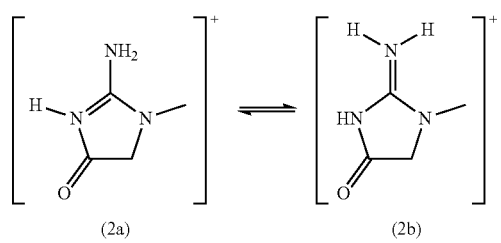

wherein the cations shown are associated with negatively charged counterions deriving from the acid used. Suitable acids for converting creatinine to activated creatinine include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, etc., as well as inorganic acids, e.g., hydrochloric acid, hydrobromic acid, sulfuric acid, nitric acid, phosphoric acid, and the like.

As alluded to above, activated creatinine can also be prepared from a protonated creatinine precursor rather than from creatinine per se. For instance, alkyl esters of creatine, e.g., creatine ethyl ester ("CEE"), shown in formula (3), can be provided as an acid addition salt using an organic acid or an inorganic acid, as above, and will readily convert in aqueous media to protonated creatinine salts (3a) and (3b) via an intramolecular nucleophilic addition reaction:

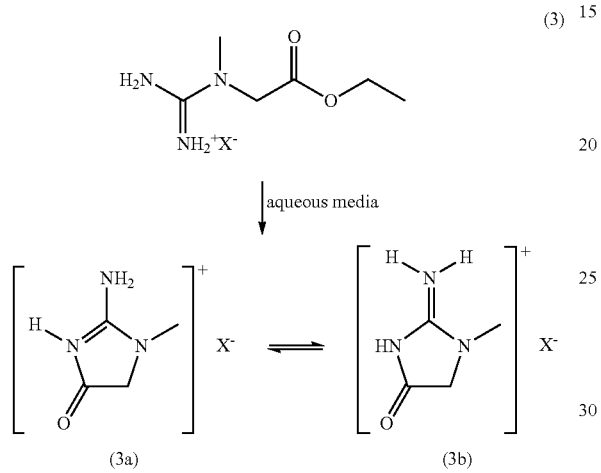

where X is an anion such as a halide, e.g., chloride, or an organic anion such as acetate, succinate, oxalate, or the like. Other creatine ester salts can also serve as precursors to activated creatinine (see, e.g., U.S. Patent Publication No. 2015/0299112 A1 to Dezard et al., incorporated by reference herein), and the invention is not limited in this regard.

In a related embodiment, an activated 2-amino-imidazol-4-one analog other than protonated creatinine serves as the antibacterial agent. The activated 2-amino-imidazol-4-one analog is represented by the resonance structures of formula (I)

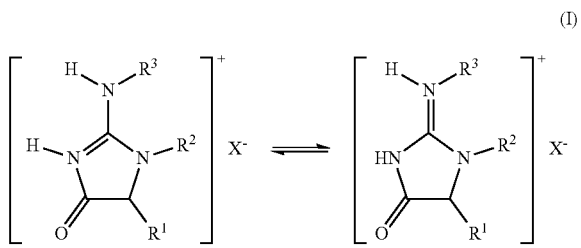

In the above structures, $R^1$ may be H (as in creatinine), or it may be halo, hydroxyl, sulfhydryl, $C_1$-$C_6$ alkyl, $C_1$-$C_6$ alkoxy, mono-($C_1$-$C_6$ alkyl)-substituted amino, and di-($C_1$-$C_6$ alkyl)-substituted amino. Preferably, $R^1$ is selected from hydrogen and $C_1$-$C_3$ alkyl.

$R^2$ in structure (I) is $C_1$-$C_6$ alkyl, preferably $C_1$-$C_3$ alkyl, while $R^3$ is selected from hydrogen and $C_1$-$C_6$ alkyl, and is preferably H or $C_1$-$C_3$ alkyl.

X is, as before, a negatively charged counterion, e.g., a halide such as chloride.

In structure (I), either $R^2$ is other than methyl or at least one of $R^1$ and $R^3$ is other than H.

Various methods of synthesizing compounds of formula (I) can be readily determined by those of ordinary skill in the art. One synthesis employs a substituted form of a creatine ester salt, e.g., the creatine ethyl ester salt (II), as the starting material, which is converted to (I) via an intramolecular cyclization reaction as described above with respect to the conversion of protonated CEE to protonated creatinine:

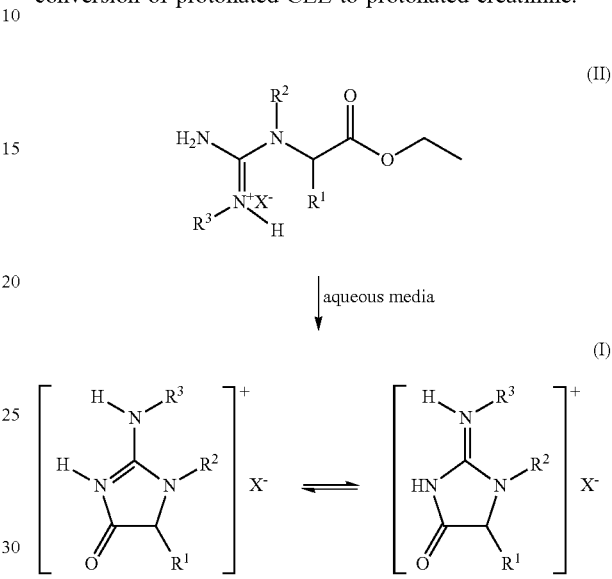

III. Pharmaceutical Formulations and Routes of Administration

The active agent combination of the invention can be formulated as an antimicrobial composition and administered to a subject as a pharmaceutical formulation. The particular form that the pharmaceutical formulation takes depends on the particular mode of administration selected and on whether the intended effect is local or systemic. Any mode of administration can be used that is appropriate in a particular case, including, but not limited to, topical, oral, parenteral (including via intravenous, intra-arterial, subcutaneous, and intramuscular injection), transdermal, intranasal, intraspinal, intravaginal, and rectal administration. Pharmaceutical formulations generally include any of a number of carriers and excipients, depending on the type of composition (e.g., cream, tablet, suppository, etc.) and the intended mode of administration (e.g., topical, oral, vaginal, etc.). Suitable formulations may be prepared using conventional methods known to those in the field of pharmaceutical formulation and described in the pertinent texts and literature, e.g., in "Remington: The Science and Practice of Pharmacy" (20th edition, A. R. Gennaro, ed., Lippincott Williams and Wilkins, 2000).

The pharmaceutical formulation may be manufactured in such a way that a unit dosage of the active agent combination is conveniently provided, i.e., a dosage suitable for single administration of a precise dosage. This may be accomplished by providing discrete dosage forms each containing a specific dose of the active agent combination, e.g., as tablets, capsules, suppositories, or the like, or by providing a drug delivery system that generates a specific single ("unit") dose upon activation, e.g., an aerosol spray, a transdermal patch, etc.

A. Topical Formulations:

In one embodiment, the active agent combination is incorporated into a pharmaceutical formulation for topical administration to be applied to a body surface, either skin, mucosal tissue, or the nails, to achieve a local, topical effect. For instance, treatment of an infection of the skin or mucosal tissue can be treated with a topical formulation. Topical formulations include ointments, creams, gels, foams, salves, lotions, pastes, solutions, sprays, as well as other compositions appropriate for topical administration. Representative topical formulations are as follows:

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations to be applied to the skin surface without friction, and are typically liquid or semiliquid preparations in which solid particles, including all active agents, are present in a water or alcohol base. Lotions are usually suspensions of solids, and preferably comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agents in the present composition in contact with the skin, e.g., methylcellulose, sodium carboxymethylcellulose, or the like.

Pastes are semisolid dosage forms in which the active agents are suspended in a suitable base. Depending on the nature of the base, pastes are divided between fatty pastes and those made from a single-phase aqueous gels. The base in a fatty paste is generally petrolatum or hydrophilic petrolatum or the like. The pastes made from single-phase aqueous gels generally incorporate carboxymethylcellulose or the like as a base.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like.

Topical pharmaceutical formulations prepared with the active agent combination may contain at least one additional pharmacologically active agent. Any such additional active agent should be appropriate for local, topical drug administration. Preferred additional agents are within the broad classes of compounds known to be topically administrable, including, but not limited to, additional topical antibiotics, additional anti-fungal agents, steroidal and nonsteroidal anti-inflammatory agents; topically active antihistamines; antipruritic agents; local anesthetics; and topical analgesic agents. Within these classes, particular attention should be paid to the inclusion of additional topical antimicrobial agents, including both antibacterial and antifungal agents, and anti-inflammatory agents. As the present composition is also useful in a method to treat acne, typically associated with the bacterium *Propionibacterium acnes*, topical pharmaceutical formulations also include anti-acne preparations. Anti-acne formulations of the invention optionally contain one or more anti-acne medicaments such as benzoyl peroxide; azelaic acid; salicylic acid; nicotinamide; a topical retinoid such as adapalene, isotretinoin, retinol, tazarotene, and tretinoin; or a topical antibiotic such as clindamycin, erythromycin, or dapsone.

Additional topical antibiotic agents include, but are not limited to, antibiotics of the lincomycin family (referring to a class of antibiotic agents originally recovered from *Streptomyces lincolnensis*), antibiotics of the tetracycline family (referring to a class of antibiotic agents originally recovered from *Streptomyces aureofaciens*), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl] amino]-1-thio-L-threo-α-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]-amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself 4-(dimethylamino)-1,4,4α,5,5α,6,11,12α-octahydro-3,6,12,12α-pentahydroxy-6-methyl-1,11-dioxo-2-naphthacene-carboxamide), chlortetracycline, oxytetracycline, tetracycline, demeclocycline, rolitetracycline, methacycline and doxycycline and their pharmaceutically acceptable salts and esters. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Additional topical antifungal agents that may be combined with the active agent combination include hamcyin, candicidin, nystatin, natamycin, amorolfine, butenafine, naftifine, terbinafine, ciclopirox, tolnaftate, undecylenic acid, and others.

The additional active agent may also be a topical anti-inflammatory agent such as a topical corticosteroid, and may be one of the lower potency corticosteroids such as hydrocortisone, a hydrocortisone-2-monoester (e.g., hydrocortisone-21-acetate, hydrocortisone-21-butyrate, hydrocortisone-2-propionate, hydrocortisone-2-valerate, etc.), a hydrocortisone-17,21-diester (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone diprionate, diflorasone diacetate, fluocinonide, mometasone furoate, triamcinolone acetonide, or the like. Alternatively, the additional active agent may be a nonsteroidal anti-inflammatory agent. Suitable nonsteroidal anti-inflammatory agents that may be used in the formulations of the present invention include, but are not limited to: propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; and combinations of any of the foregoing.

Additional active agents that can be advantageously incorporated into topical formulations with the present active agent combination include, solely by way of example, the following: topically active antihistamines such as bamipine, chloropyramine, chlorphenoxamine, clemastine, diphenhydramine, dimetindene, mepyramine, and promethazine; antipruritic agents such as the counterirritants mint oil, menthol, and camphor; local anesthetic agents such as phenol, benzocaine, lidocaine, prilocaine and dibucaine; and topical analgesics such as glycol salicylate, methyl salicylate, 1-menthol, d,l-camphor and capsaicin.

B. Formulations for Systemic Administration:

For systemic drug administration, antimicrobial compositions containing the active agent combination of the invention can be formulated for administration by any route appropriate for the particular infection, e.g., via the oral, parenteral, rectal, vaginal, buccal, sublingual, nasal, or transdermal routes, or by inhalation or using an implanted reservoir.

Depending on the intended mode of administration, antimicrobial compositions of the invention intended for systemic administration may be a solid, semi-solid or liquid, such as, for example, a tablet, a capsule, a caplet, a liquid, a suspension, an emulsion, a suppository, granules, pellets, beads, a powder, or the like, preferably, although not necessarily, in unit dosage form suitable for single administration of a precise dosage. As noted earlier, suitable pharmaceutical formulations and dosage forms may be prepared using conventional methods described, for instance, in Remington's, supra. For those active agent combinations that are orally active, oral dosage forms are generally preferred, and include tablets, capsules, caplets, solutions, suspensions and syrups, and may also comprise a plurality of granules, beads, powders, or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms for those active agent combinations that are orally active, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like.

Oral dosage forms, whether tablets, capsules, caplets, or particulates, may, if desired, be formulated so as to provide for controlled release of the antimicrobial agent combination, where controlled release may be sustained release, delayed release, or a combination thereof. Controlled release formulations are preferably sustained release, meaning gradual delivery of the antimicrobial agent combination over an extended time period. Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile aqueous and nonaqueous solutions, suspensions, and emulsions. Injectable aqueous solutions contain the antimicrobial agent combination in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The antimicrobial active agent combination of the invention may also be administered through the skin or mucosal surface using conventional transdermal drug delivery systems, wherein the active agent may be contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition, the active agent combination of the invention may be formulated as a depot preparation for controlled release of the active agents, preferably sustained release over an extended time period, as explained above. These sustained release dosage forms are generally administered by implantation (e.g., subcutaneously or intramuscularly or by intramuscular injection). The depot may be composed of a controlled release matrix that gradually dissolves and/or erodes in the presence of aqueous body fluids to release the active agent combination slowly, over a prolonged time period.

An additional pharmacologically active agent can be incorporated into a pharmaceutical formulation of the invention for systemic drug administration. The additional active agent may include an additional antibacterial agent and/or an additional antifungal agent, or another active agent typically chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-inflammatory agents; antinauseants; antipruritics; antipsychotics; antipyretics; antispasmodics; antitubercular agents; antiulcer agents; antiviral agents; anxiolytics; appetite suppressants; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypoglycemic agents; immunosuppressive agents; leukotriene inhibitors; mitotic inhibitors; muscle relaxants; narcotic antagonists; nutritional agents, such as vitamins, essential amino acids and fatty acids; parasympatholytics; psychostimulants; sedatives; steroids; sympathomimetics; and vasodilators including general coronary, peripheral and cerebral. The additional pharmacologically active agent may also be a biomolecule, e.g., a molecular moiety selected from DNA, RNA, antisense oligonucleotides, peptidyl drugs, i.e., peptides, polypeptides and proteins (including fluorescent proteins), ribosomes and enzyme cofactors such as biotin.

The combination of the imidazole antifungal agent and the activated creatinine or other activated 2-amino-1-imidazol-4-one analog together represent, in general, in the range of about 5 wt. % to about 99.5 wt. % of the total pharmaceutical formulation, typically in the range of about 3 wt. % to about 99.5 wt. %. With an aqueous pharmaceutical formulation, the combination of the imidazole antifungal agent and the activated creatinine or other activated 2-amino-1-imidazol-4-one analog is present in a concentration in the range of about 10 mM to about 2 M, preferably in the range of about 100 mM to about 2 M.

In any of the above-described pharmaceuticals formulations, whether for topical or systemic delivery, nanotechnology may be advantageously employed to prepare the antimicrobial agent combination in the form of nanoparticles, nanofibers, nanobeads, nanoparticle matrices or clusters, and the like. These may be formulated for controlled release, e.g., sustained release and/or delayed release, of the active agent combination. Nanoparticle-type formulations may also comprise nanoparticles, nanofibers, nanobeads, nanoparticle aggregates, etc., that are functionalized so as to contain a targeting moiety such as an antibody or antibody fragment that has affinity for a particular type of cell and/or biomolecule.

IV. Treatment of Infections

The invention provides a method for treating a bacterial infection in a subject by administering an antibacterially effective amount of a combination of an imidazole antifungal agent and activated creatinine, wherein the imidazole antifungal agent represents in the range of about 0.5 mol % to about 30 mol % of the combination of the antifungal agent and the activated creatinine. In a preferred embodiment, the imidazole antifungal agent represents in the range of about 0.5 mol % to about 20 mol % of the combination of the antifungal agent and the activated creatinine. The infection may involve either gram-positive bacteria or gram-negative bacteria, and/or the bacteria may have developed antibiotic-resistance and/or be refractory to known antibiotic agents.

The invention provides an analogous method for treating a fungal infection in a subject, in which an antifungally effective amount of a combination of an imidazole antifungal agent and activated creatinine is administered to the subject, wherein the proportion of the two active agents is as provided above and as described in detail in Section II.

The invention additionally provides an analogous method for treating a viral infection in a subject, in which an effective antiviral amount of a combination of an imidazole antifungal agent and activated creatinine is administered to the subject, wherein the proportion of the two active agents is as provided above and as described in detail in Section II.

In a related embodiment, a different activated 2-amino-imidazol-4-one analog (i.e., an activated 2-amino-imidazol- 4-one other than activated creatinine) is substituted for activated creatinine in either the antibacterial or the antifungal context. The activated 2-amino-imidazol-4-one analog is an acid addition salt of a 2-amino-imidazol-4-one analog, having the structure of formula (I)

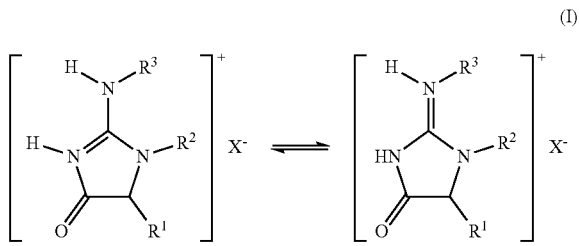

where $R^1$, $R^2$, $R^3$, and X are as defined previously.

Bacterial infections that can be effectively treated with the present active agent combination include organisms within the genera *Acinetobacter, Actinobacteria, Bacillus, Enterobacter, Enterococcus, Escherichia, Haemophilus, Klebsiella, Proteus, Pseudomonas, Staphylococcus*, and *Streptococcus*. Examples within the aforementioned genera, include, but are not limited to, those described in U.S. Patent Publication No. 2013/0243847 A1 to McDonald et al. As explained in the aforementioned patent application, antibacterially activated creatinine has shown broad spectrum inhibitory activity with respect to both gram negative and gram positive bacteria, including *Staphylococcus aureas, Enterococcus faecalis, Pseudomonas aeruginosa, Pseudomonas fluorescens, Escherichia coli, Acinetobacter baumannii, Brevibacterium linens, Micrococcus luteus, Bacillus subtilis*, and *Bacillus cereus*, as well as antibiotic resistant organisms that include methicillin-resistant *Staphylococcus aureas* (MRSA), *Acinetobacter baumannii* high level resistance (HLR), *E. coli* beta lactamase producer, *Pseudomonas aeruginosa* HLR, and vancomycin-resistant enterococci (VRE), the most common causes of which are *E. faecium* and *E. faecalis*. It should be noted that *A. baumannii, P. aeruginosa*, Enterobacteriaceae (including *Klebsiella* and *E. coli*), *E. faecium*, and *S. aureas* are among those that have been designated as antibiotic-resistant "priority pathogens" by the World Health Organization, i.e., bacteria that currently pose the greatest threat to human health. See the World Health Organization news release dated 27 Feb. 2017, entitled "WHO Publishes List of Bacteria for which New Antibiotics Are Urgently Needed."

*Streptococcus pyogenes* and *Streptococcus pneumoniae* are also bacteria against which the present active agent combination is effective. The composition of the invention thus acts as a broad spectrum antibacterial formulation, killing both gram positive and gram negative bacteria, bacteria that can be classified as motile, drug-resistant, rods, and cocci, and, importantly, drug-resistant bacteria. In treatment of bacterial infections, the present composition may be administered in conjunction with an additional antibacterial agent, which may or may not be incorporated into a composition together with the antimicrobial agent combination. Examples of such additional antibacterial agents are set forth in Section III.

In addition to treating systemic bacterial infections, the present compositions can also be used to treat topical bacterial infections, e.g., acne vulgaris ("acne") and bacterial infections secondary to diaper rash in infants.

The fungal infections that may be treated using the present compositions include local and systemic infections with any type of fungal pathogen, including yeast fungi and mold fungi. For use in treating fungal infections, the compositions of the invention may be administered in any of the dosage forms using any of the modes of administration mentioned or described in the preceding sections. The fungal infections include infections of the body surface and internal infections. Common fungal infections are infections of the skin, scalp, nails, mouth, and vagina. The most common pathogens associated with fungal infections are those in the *Candida* genus, referred to as thrush when the infection is in the mouth and as a yeast infection when it affects the vagina. Candidiasis also occurs elsewhere in the body, such as the GI tract, the urinary tract, and the respiratory tract. *Candida* infections that can be treated using the present invention include, by way of example rather than limitation, *C. albicans, C. bracarensis, C. parapsilosis, C. glabrata, C. guilliermondii, C. krusei, C. lusitaniae, C. tropicalis*, and *C. utilis*. Other common fungal infections that can be treated using the present active agent combination are those in the *Aspergillus* genus, such as *A. niger, A. claviatus, A. fischerianus, A. flavus*, and *A. fumigatus*; those of the genus *Trichophyton* such as *Trichophyton rubrum, Trichophyton mentagrophytes, Trichophyton verrucosum, Trichophyton tonsurans, Trichophyton equinum, Trichophyton kanei, Trichophyton raubitschekii*, and *Trichophyton violaceum*; those of the genus *Microsporum* such as *Microsporum gypseum, Microsporum audouinii, Microsporum nanum, Microsporum versicolor, Microsporum equinum*, and *Microsporum canis*; those of the genus *Malassezia* such as *Malassezia pachydermatis*; those of the genus *Epidermophyton*, such as *Epidermophyton floccosum*; and many others.

A topical formulation containing the present composition, i.e., the active agent combination discussed throughout this disclosure can be applied to a body surface to counteract infection of the skin, scalp, and nails. One such application involves treatment of fungal infection in the dermatophyte category; dermatophytes, as is well known, cause fungal infections of the skin. Examples of dermatophytes are the tinea group of fungi. These include, without limitation: athlete's foot, also known as tinea pedis, a common fungal infection of the foot; tinea unguium, an equally common fungal infection of the nails; tinea corporis, a fungal infection on the skin of the arms and legs (also known as "ringworm"); and tinea capitis, a fungal infection of the scalp. In treating a tinea infection, the present composition is optionally administered in conjunction with an additional antifungal agent effective against these fungi, such as terbinafine (commonly prescribed for athlete's foot); amorolfine, efinaconazole, and ciclopirox (prescribed for nail fungi); and griseofulvin (most commonly prescribed for tinea corporis and tinea capitis).

For treatment of vaginal yeast infections, administration is typically intravaginal, and the formulation type is generally a cream, gel, ointment, or pessary. For treatment of oral yeast infections, the active agent combination can be incorporated into an oral gel, a lozenge, a buccal formulation, or a liquid. For treatment of internal and/or systemic fungal infections, such as may be caused by fungi in the *Aspergillus, Candida*, and Creptococcus families, and administration of the present compositions is carried out systemically, using any of the systemic routes of administration described in Section III, such as oral or parenteral administration.

When an infection involves bacterial colonization of a body orifice and the adjacent tissue of a subject, treatment or prophylaxis can be carried out by delivering to the body orifice and/or adjacent tissue an antimicrobial active agent combination of the invention prepared as a topical formulation or suppository, as described in the preceding section. This method may be applied to treat or prevent bacterial colonization of a subject's nasal cavity, ear canal, lip, urethra, vagina or rectum. The preferred route of delivering the antibacterial agent in practicing the method is by spray, swab, drops, suppositories, foams, or wash. For treating or preventing bacterial colonization of the nasal cavity, the antibacterial composition is advantageously delivered by inhalation or by spraying, preferably in powder form. An aerosolized bolus containing the present composition may be prepared using conventional means, e.g., by admixture with a pharmaceutically acceptable bulking agent and optionally an aerosol propellant. In another example, the present composition may be used to treat *Clostridium difficile* (also known as *C. difficile, C. diff* or CDF) infections of the colon, which are frequent in immunosuppressed patients. The composition of the invention might be incorporated into a suppository, foam, ointment, or other formulation and deployed deep in the colon to treat a *C. difficile* infection, and/or prevent infection from recurring. For vaginal or rectal administration, suppositories formulated with the present compositions are preferred.

The dosage regimen for treatment of either a bacterial infection or a fungal infection will depend on a number of factors that may readily be determined, such as the particular bacterium, the severity of the infection, and the responsiveness to treatment. Administration may be on an as-needed basis but normally involves periodic and regular administration within the context of an ongoing dosage regimen. As such, administration will normally involve one or more doses per day, with a course of treatment lasting from several days to several months, or until a cure is effected or significant progress is made in eliminating the infection. One of ordinary skill may readily determine optimum dosages, dosing methodologies and repetition rates. For topical administration, it is contemplated that the composition will be applied one to four times daily.

Administration of the antimicrobial active agent combination to treat a bacterial infection will generally be carried out using a pharmaceutical formulation or dosage form appropriate to a particular route of administration, as explained in the preceding section. For example, a topical formulation such as an ointment, cream, or gel, is appropriate to treat a topical infection, while to treat a bacterial infection of the nasal passages, a composition for intranasal administration (e.g., a nasal spray) is used.

In another embodiment, the invention provides a method for treating an individual who has both a bacterial infection and a fungal infection, by administering to the individual an effective amount of an antimicrobial active agent composition of the invention. Mixed bacterial-fungal infections are not unusual, and are seen in different patient populations, for different reasons, and in different areas of the body. For example, it has been reported that progression of the genetic disease cystic fibrosis (CF), in the respiratory tract, may involve fungal as well as bacterial pathogens, and many CF patients exhibit airway infections in which both bacteria and fungi are present. See Whitaker et al. (2010) *Med. Mycol.* 48 (Supplement 1): S125-S132. As another example, a high incidence of vulvovaginal yeast infections has been found in women with recurrent bacterial vaginosis, with both the fungal and bacterial entities simultaneously present. Redondo-Lopez et al. (1990) *Sex. Transm. Dis.* January-March; 17(1):5103. In addition, patients who are immunosuppressed, as a result of autoimmune disease, transplant surgery, or non-autoimmune inflammatory diseases, frequently exhibit both bacterial infections and fungal infections simultaneously. Furthermore, an unfortunate consequence of some antibacterial regimens is that the body's resistance to other types of infection, including fungal infection, decreases. For instance, suppression of bacteria using antibiotic therapy is known to increase the likelihood of vaginal yeast infections.

Accordingly, in a related embodiment, the invention provides a method for treating an individual who has been undergoing treatment for a bacterial infection with antibiotics, and the composition of the invention is administered to prevent or treat a fungal infection that may be incurred as a result.

V. Treatment of Inflammation

In a further embodiment, the invention provides a method for treating inflammation in a patient. The inflammation may be associated with an infection, e.g., a bacterial infection and/or a fungal infection. Inflammation, both acute and chronic, is a complex biological response of the body's immune system to invading pathogens of all types. It is widely accepted that infectious diseases can be exacerbated by an excessive inflammatory response, and, in severe cases, it is often the number and/or extent of the inflammatory responses that bring about the patient's death rather than the infecting pathogen. This is the case with sepsis, for example, when a patient's inflammatory response to a bacterial and/or viral infection is extreme and results in tissue and organ damage.

A method is accordingly provided for treating inflammation associated with, e.g., caused by, a bacterial infection, a fungal infection, or both a bacterial infection and a fungal infection. The method for treating such inflammation involves administration of an activated creatinine/imidazole antifungal agent combination with the mole ratio of the two active agents in the combination as described in previous sections. In this embodiment, it will be appreciated that the present composition facilitates simultaneous treatment of inflammation and the bacterial and/or fungal infection associated therewith.

The method may be used as adjunctive therapy to a pre-existent or simultaneously begun anti-inflammatory regimen, and/or one or more anti-inflammatory agents, including steroidal and nonsteroidal anti-inflammatory agents, can be incorporated into a pharmaceutical formulation containing the active agent combination of the invention.

VI. Wound Dressings and Treatment of Wounds

An important application of the present composition is in the treatment of wounds. By "wound" is meant an injury to any body tissue, and the wounds that are treatable with the present methods and compositions include acute, subacute, and chronic wounds, where the wounds may be open or closed. Examples of wounds that can be effectively treated with the compositions and methods of the invention include burns, incisions, lacerations, abrasions, puncture or penetrating wounds, surgical wounds, contusions, hematomas, crushing injuries, and ulcers. Wounds include injuries to the skin and subcutaneous tissue caused in any number of different ways, e.g., pressure sores from extended bed rest and wounds induced by trauma, and have varying characteristics. Wounds may be classified into one of four grades depending on the depth of the wound: Grade I, wounds limited to the epithelium; Grade II, wounds extending into the dermis; Grade III, wounds extending into the subcutaneous tissue; and Grade IV, or "full-thickness" wounds, wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. Deep wounds refer to both Grade III and Grade IV wounds, while chronic wounds refer to wounds that have not healed, and include venous ulcers, pressure sores, vasculitic ulcers, diabetic ulcers and decubitus ulcers. Chronic skin wounds include, by way of example, pressure ulcers, diabetic ulcers, venous ulcers, vasculitic ulcers, arterial ulcers, and mixed ulcers. The compositions and methods of the present invention contemplate treating all wound types, including deep wounds and chronic wounds.

The active agent combination of the invention can be used as a wound healing formulation and applied either internally or externally, and may be directed towards any tissue exhibiting a wound. The composition may be in the form of a liquid preparation or a semi-solid or solid composition, for direct application, or the composition may be incorporated into a wound dressing material such as those described in U.S. Patent Publication No. 2013/0243847, previously incorporated by reference. Wound dressing materials include, by way of example: hydrocolloid dressings; hydrogel dressings; transparent films; foams; alginates; absorptive dressings; dressings of woven and nonwoven fabrics, including gauzes; and bandages. The selection of a particular wound dressing materially is normally made on the basis of functionality in a particular circumstance, with respect to, for instance, absorption of wound exudate, control of bleeding or fluid loss, maintenance of a moist wound surface, protection against contamination, desiccation and abrasion.

Hydrocolloidal wound dressing materials are biodegradable dressings that are absorbent and adhere directly to the body surface, and are thus composed of an absorbent material and skin contact adhesive. Carboxymethylcellulose, pectin, and/or gelatin are commonly used as the dressing materials. Hydrocolloid dressings are moisture retentive and promote autolytic debriding. They are also highly occlusive, providing protection against exogenous contaminants. They are available in wafer form in a variety of shapes, as well as granules, powders and paste. Representative examples of dressings of this type include Comfeel Plus, Duoderm, Granuflex, and Tegaderm. See also, U.S. Pat. Nos. 6,033,684, 4,551,490 and 4,393,080. Hydrocolloid dressings may be secured to a wound site by means of a transparent film cover that is impermeable to liquid, bacteria and viruses. Alternatively, the hydrocolloid wound dressing material may be laminated to a backing film. As explained in U.S. Pat. No. 4,551,490, a hydrocolloid wound dressing may be produced from at least one finely divided or granular, water-soluble and/or water-swellable absorbent material dispersed in a pressure-sensitive, synthetic or natural elastomeric binder (e.g., polyisobutylene, isobutylene copolymers, styrene-butadiene rubber, etc.), with the antimicrobial composition of the invention incorporated therein, in an amount that results in a final wt. % of 5-10 based on the total weight of the hydrocolloid dressing. Typically, a layer of the aforementioned antimicrobial hydrocolloid composition is disposed on a thin, pliable, water-insoluble support film to yield the finished product. Optional components in the hydrocolloid dressing include tackifiers, plasticizers, stabilizers, and the like.

A hydrogel can be described generally as an insoluble polymer with hydrophilic sites that absorb and interact with significant volumes of liquid, particularly water or in the case of wound dressings, wound exudate. A hydrogel-based wound dressing material typically comprises cross-linked hydrophilic macromolecules containing up to about 95% water by weight. These dressings are effective for establishing and maintaining a moist microenvironment for cell migration and rehydrating eschar and slough for easy removal from the wound. They also diminish wound pain. Representative examples of hydrogel dressings include, without limitation, Solosite, IntraSite and Carrasyn products. See also, U.S. Pat. Nos. 6,238,691, 5,112,618, 5,106,629 and 4,909,244. The hydrogel material may be in sheet or gel form, and in the latter case can be applied directly to the wound, or impregnated in an absorbent compress, e.g., gauze, which is used for dressing the wound. The absorbent compress may be bound to the wound by a suitable bandage material.

Alginate wound dressings comprise non-woven fibers of soluble salts of alginic acid, a derivative of seaweed. These dressings are moisture-retentive, non-occlusive and non-adherent, and are capable of absorbing moderate to heavy wound exudates in superficial and deep wounds. They are available in pad (felt) and rope form, the latter being useful as a filler for deep or tunneling wounds. Representative examples of such dressings include, without limitation, Kaltostat™ and Curasorb®. See also U.S. Pat. Nos. 5,836,970, 5,197,945, 4,948,575 and U.S. Patent Publication No. 2005/0287193 A1.

In another embodiment, the wound dressing may be in the form of a bandage strip and an absorbent compress attached to the bandage strip. This form of dressing is commonly referred to as a first aid field dressing. Preferably, the absorbent compress is a gauze, e.g., cotton or a chemical derivative of cellulose, or an open cell foam material, e.g., hydrophilic polyurethane foam, optionally gel film or silicon coated. A wound dressing of this type may be applied as a dry dressing or a water dressing, i.e., a dressing that is kept wet with sterilized water or saline solution prior to use. It is conventionally packaged in an air-tight container.

The wound dressing may also be embodied in an adhesive bandage comprising a flexible substrate coated with a pressure-sensitive adhesive coating and an absorbent compress affixed to at least part of the adhesive coated substrate, with the absorbent compress having incorporated therein the antimicrobial composition of the invention. The flexible substrate may be a plastic or fabric film, which is in the form of a strip, a patch or a spot. The invention may also be incorporated into pre-surgical bandages used to sterilize the intended incision site.

These wound dressings facilitate wound care by protecting against bacterial colonization within the dressing and bacterial penetration through the dressing. This protective effect is a direct result of the barrier function imparted by the antimicrobial composition of the invention. VII. Disinfection:

In another embodiment, the antimicrobial active agent combination of the invention is used as a disinfectant composition to sanitize an inert surface, in the residential, commercial, or industrial contexts, as well as in hospital settings. The active agent combination can be formulated into a disinfectant composition along with other suitable components such as a liquid carrier, detergents, other antimicrobial agents, emollients, skin protectants, buffer systems, or other components, and then packaged into wipes, gel tubes, spray bottles, or the like. The disinfectant composition so prepared and packaged may be used to sanitize inert surfaces such as those of hospital beds and tables, operating room equipment, surgical instruments and other medical devices, medical gloves, catheters, dental instruments, food and water treatment equipment, agricultural processing equipment, and in any other context where disinfecting a surface is advantageous or necessary.

The present formulation can be combined with a relatively volatile disinfectant or sterilizer, to lower the overall volatility of the composition. This, in turn, increases efficacy of a disinfectant or sterilizer applied to a surface, as a decrease in volatility provides for a longer lasting surface residue.

VIII. Other Products and Uses

As an effective antimicrobial formulation, the composition of the invention is also useful in imparting antimicrobial properties to fibrous articles, including fibers, threads, yarns, woven fabric and non-woven fabric. These fibrous articles may be used for the manufacture of any number of finished goods including, without limitation, an absorbent compress, a bandage, a wound packing material, a garment, bed clothes, a dust cloth, a tampon, a sanitary napkin and a fluid filter. The antimicrobial woven and non-woven fabrics made in this way can be used to manufacture garments such as surgical gowns, foot protectors, face masks, head or hair coverings, diapers, and gloves. Antimicrobial fibrous materials containing the present composition may also be used in the manufacture of paper, cardboard, pressed wood or fiberboard according to methods conventionally used for the manufacture of such products.

The present composition can also be embodied in a wide variety of personal care products that comprise an antimicrobially effective amount of the composition. Examples of such products include, without limitation, skin care products, hand sanitizers, body lotions, feminine care products, foot care products, deodorants, and dental care products. The products are packaged in containers appropriate to their intended use, e.g., bottles that include a pump dispenser or a spray nozzle, an aerosol dispenser, a roll-on dispenser, a stick dispenser, etc.

Antibacterial protection in deodorants is advantageous insofar as it enhances personal hygiene by controlling the growth of odor-causing bacteria. In soaps and body washes, the antimicrobial agent combination can be incorporated to facilitate killing or controlling bacteria that can cause illnesses, odor, and/or skin infections. In this embodiment, as a non-limiting example, the antimicrobial compositions of the invention may be used in a method of suppressing or preventing formation of body odor, due to odor-causing bacteria, by applying to at least one body part affected by body odor, e.g., the axilla or feet, an antimicrobial composition as described herein.

Unlike ordinary soap products, formulations prepared using the present agent combination leave a residual amount of the agents on the skin after rinsing, which, in turn, helps to inhibit growth of any remaining bacteria. Hand sanitizers formulated with the present composition provide a similar advantage, and are convenient when washing with soap and water isn't possible. Antimicrobial lotions formulated with the present active agent combination moisturize rough, dry skin and offer added protection by controlling bacteria. As with antimicrobial soaps, washes, and hand sanitizers, a small amount of the antimicrobial components in a lotion will remain on the skin for an extended period of time and thus assist in inhibiting the growth of bacteria. Antimicrobial dental products formulated with the present antimicrobial composition, e.g., mouthwashes, rinses, and toothpastes, help to reduce to reduce bacteria in the mouth that may lead to plaque formulation or gum diseases such as gingivitis.

The skin care products may also include an effective amount of a therapeutic agent for the treatment of a bacterially mediated dermatological condition. Among the conditions that may be treated with the skin care products of the invention are inflammatory dermatoses, such as acne vulgaris, rosacea, atopic dermatitis and other forms of eczema, as well as impetigo, bacterial folliculitis, furunculosis, carbunculosis, ecthyma, erysipelas, and cellulitis.

The present composition also finds utility as an antimicrobial-type preservative in the areas of cosmetics and cosmeceuticals, including, without limitation: in make-up such as foundation base or primer foundation, concealer, blush, powder, lipstick, lip gloss, eye shadow, eye liner, mascara, and body make-up; in cosmeceuticals for facial application such as facial creams, masks, scrubs, and cleansers; and in other products applied to the skin such as sunscreens, oils, gels, creams, foams, and pastes.

The active agent combination of the invention can also be employed as a preservative, e.g., in packaging, food products, etc., such as by coating the packaging or food product and/or incorporation therein; in the treatment of wood and other materials that are attacked and degraded by fungi; in aspects of gardening and agriculture, for instance in the treatment of plants, fruits, and vegetables, in which case the composition of the invention can be applied to a surface and/or the roots of a plant; in public health contexts such as water treatment and sewage processing; in any packaging wherein a sterile local environment should be maintained; wherever bacteria or fungi may degrade a host medium; wherever an antimicrobial effect is needed without risk of a substantial adverse impact on the environment or ecosystem; wherever an antimicrobial effect is needed in which the risk of developing drug resistance is nonexistent or minimal.

The compositions and methods of the invention are, accordingly, of enormous potential importance in many fields.

It is to be understood that while the invention has been described in conjunction with a number of specific embodiments, the foregoing description as well as the examples that follow are intended to illustrate and not limit the scope of the invention. Other aspects, advantages and modifications will be apparent to those skilled in the art. All patents, patent applications, and publications mentioned here are hereby incorporated by reference in their entireties.

EXPERIMENTAL

Example 1—Preparation of Clotrimazole/Activated Creatinine Formulations

Formulations of the invention were prepared containing clotrimazole (Chem-Impex International, Inc., Wood Dale, Ill.) and creatinine hydrochloride (Sigma-Aldrich Corporation, St. Louis, Mo.) in different molar ratios, in order to evaluate the potential effect of those ratios on antibacterial efficacy. The formulations were prepared by combining clotrimazole with creatinine HCl in varying relative amounts to produce solutions containing 3 mM clotrimazole and activated creatinine (i.e., creatinine hydrochloride) in a concentration ranging from 0 mM to 350 mM. The specific procedures used were the following:

A 3 mM clotrimazole solution was made by adding 5.0 mg clotrimazole to 1.0 ml of polyethylene glycol 400

("PEG-400"; Sigma-Aldrich), and then, while mixing by vortexing), 4.0 ml of purified water and 100 µl of 0.05N HCl were added to the mixture. This yielded a 1.0 mg/ml clotrimazole solution, i.e., a 0.1% solution of clotrimazole in 20% PEG-400 and 0.001N HCl, pH 4.5. The 1 mg/ml clotrimazole solution, it will be appreciated, is equivalent to a 3 mM solution.

The creatinine HCl stock solution was made by dissolving creatinine HCl in purified water to provide an aqueous solution having a concentration of 20% Creatinine hydrochloride, equivalent to a 200 mM creatinine HCl solution.

In formulating the combined clotrimazole/activated creatinine solutions, the above procedure for preparing the 3 mM clotrimazole solution was followed, except that the 4 ml of purified water added during vortexing was replaced with "x" ml of purified water and "4.0-x" ml of the creatinine HCl stock solution. In this manner, clotrimazole/activated creatinine solutions were prepared where the amount of clotrimazole in the clotrimazole/activated creatinine mixture, in terms of mol %, was 0% (as a control), 0.8%, 1.0%, 1.1%, 1.7%, 3.3%, 6.4%, 14.3%, and 100%; see FIG. 1.

Example 2—Antibacterial Evaluation: S. aureas, E. coli, and E. faecalis

The antibacterial activity of the clotrimazole/activated creatinine solutions prepared as described in Example 1 was evaluated with respect to Staphylococcus aureus (Gram positive; laboratory strain 29213), E. coli (Gram negative; laboratory strain 35150), and a multiple drug resistant strain of Enterococcus faecalis (Gram positive). The S. aureus and E. coli were purchased from the American Type Culture Collection, and the E. faecalis was a local veterinary clinic isolate. The minimum inhibitory concentration ("MIC") for each solution was determined against each of the three bacteria after incubation for 24 hours at 37° C. using two-fold dilutions and flat-bottom 96-well plates.

Figure 2B:
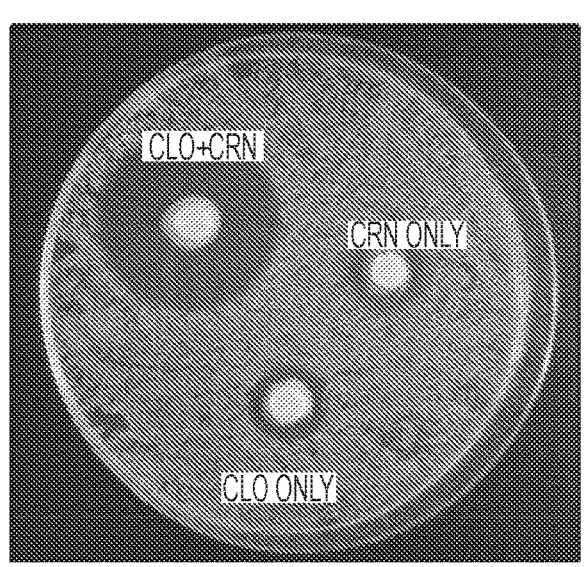

FIG. 1 is a bar graph of the results, and illustrates the variation in MIC as a function of the percent, by mole, of clotrimazole in the clotrimazole/activated creatinine mixture. MIC is expressed as mg/ml. For S. aureus, the MIC dropped from 10.9 mg/mL with activated creatinine alone to 1.4-2.7 mg/mL (a 4.0-fold to 7.8-fold change) with all of the clotrimazole/activated creatinine combination solutions. For E. coli, the MIC dropped from 21.9 mg/mL with creatinine hydrochloride alone to 4.8 mg/mL (a 4.6-fold decrease) with 1 mol % clotrimazole in the clotrimazole/activated creatinine. For E. faecalis, the MIC dropped from 21.8 mg/mL with activated creatinine alone to 4.8 mg/mL (a 4.5-fold decrease) with 1 mol % clotrimazole in the clotrimazole/ activated creatinine mixture. For each bacterium, the synergistic effect is seen at lower mol % clotrimazole values and diminishes at higher mol % clotrimazole values. Clotrimazole alone (without creatinine hydrochloride, i.e., at 100 mol % clotrimazole) had no impact on bacterial growth. In FIG. 2, photographs of the comparative effects of the composition of the invention versus clotrimazole alone and creatinine hydrochloride alone; FIG. 2A shows the results with S. aureas and FIG. 2B shows the results with E. faecalis.

These unexpected results thus indicate that a clotrimazole/activated creatinine mixture has surprisingly greater antibacterial efficacy than either component alone, particularly within a certain range of clotrimazole/[clotrimazole plus activated creatinine] values. There is no prior teaching or suggestion to decrease the MIC of activated creatinine against bacteria, i.e., to increase the antibacterial efficacy of activated creatinine, by combining it with an antifungal agent such as clotrimazole, nor is there any prior teaching or suggestion to render clotrimazole antibacterial by combining it with activated creatinine. It is also important to note that the combination exhibits this synergy with respect to not only the representative bacteria S. aureus and E. coli but also the drug-resistant bacterial strain tested, E. faecalis.

Example 3—Antifungal MIC Evaluation: Saccharomyces Spp. and Candida albicans

The antifungal activity of the clotrimazole/activated creatinine solutions prepared as described in Example 1 was evaluated with respect to Saccharomyces spp. yeast (baker's yeast) and Candida albicans yeast (from the American Type Culture Collection, ATCC1023). The MIC for each solution was determined against the fungi after incubation for 24 hours at 37° C. using two-fold dilutions and flat-bottom 96-well plates.

The results are set forth in FIG. 3, which illustrates the variation in MIC as a function of the percent, by mole, of clotrimazole in the clotrimazole/activated creatinine mixture. MIC is expressed as mg/ml. For Saccharomyces yeast, the MIC dropped from 7.5 with clotrimazole alone to 0.94 (an 8-fold change) with 0.8 mol % clotrimazole to 1.7 mol % clotrimazole in the mixture. For C. albicans yeast, the MIC dropped from 6.0 with clotrimazole alone to 1.3 (a 4.6-fold change) with 0.8 mol % clotrimazole in the mixture. Beyond these low points in the MICs for each of the fungi, the synergistic effect diminishes as the mol % clotrimazole is increased. It should be noted that activated creatinine alone, i.e., without clotrimazole, had no impact on fungal growth.

Although clotrimazole is known as an effective antifungal agent, combining clotrimazole with activated creatinine to enhance clotrimazole's antifungal activity is unknown and provides an unexpected benefit. It is particularly surprising that enhancement of antifungal activity is seen with low concentrations of clotrimazole, when activated creatinine alone exhibited no antifungal effect. It is also unexpected that the synergistic effect should occur within a relative small range of clotrimazole/activated creatinine ratios, and that above this range, antifungal efficacy decreases as the percentage of clotrimazole in the clotrimazole/activated creatinine combination increases.

Example 4—Comparative Antifungal Testing: Mold Fungi

Two species of penicillium, Penicillium spp. 1 and Penicillium spp. 2, were isolated from contaminates that grew on laboratory plates and were grown in LB broth, shaking for three days. One hundred microliters of the fungal broth were added to an LB agar plate and evenly spread on the surface. Test samples containing the following aqueous solutions were prepared:

0.1% (w/v) clotrimazole (3.4 mM);
0.1% (w/v) clotrimazole in 200 mM creatinine ethyl ester hydrochloride ("CEE") (3.4 mM in clotrimazole; 1.7 mol % clotrimazole in the clotrimazole-creatinine mixture);
0.1% (w/v) ketoconazole (5.3 mM);
0.1% (w/v) fluconazole (30 mM).

The test samples were added to the wells and analyzed for inhibition of fungal growth after 48 hours. As is known in the art, CEE cyclizes to give creatinine in aqueous conditions; see, e.g., Giese et al. (2009) Biochem. Biophys. Res. Comm. 388(2):252-255.

The test results are shown in FIG. 4, a photograph illustrating the comparative antifungal effects of a clotrimazole/activated creatinine composition versus 0.1% (w/v) solutions of ketoconazole, clotrimazole, and fluconazole. The left portion of FIG. 4 illustrates the results obtained for *Penicillium* spp. 1 and the right portion of FIG. 4 shows the results with *Penicillium* spp. 2. These results indicate that the synergistic effect with regard to enhancement of CLO antifungal activity applies to mold fungi as well as yeast fungi. It is unexpected that blending CLO with Creatinine hydrochloride can result in a formulation that inhibits growth of *penicillium* mold fungi when, as may be seen in FIG. 4, CLO alone and other antifungal agents alone do not. It is anticipated that MICs for various CRN/CLO blend ratios versus mold fungi will vary in a manner similar to the MICs of these ratios found versus yeast fungi.

Example 5—Comparative Antifungal Testing: Yeast *Saccharomyces* Spp.

One gram of commercially available over-the-counter cream containing 1 wt. % clotrimazole was thoroughly mixed with 2.5 g PEG-400 and 6.5 g water. This 1:10 (0.1%) clotrimazole formulation was tested for antifungal activity by placing approximately 50 microliters onto an LB agar plate that was previously spread with a test organism, yeast *Saccharomyces* spp. Creatinine hydrochloride was added to a portion of the clotrimazole mixture to yield a 200 mM final concentration. The clotrimazole-creatinine hydrochloride was 3.4 mM in clotrimazole, with 1.7 mol % of clotrimazole in the clotrimazole-creatinine mixture. The formulation was tested for antifungal activity as for the clotrimazole-only formulation.

Figure 5A:
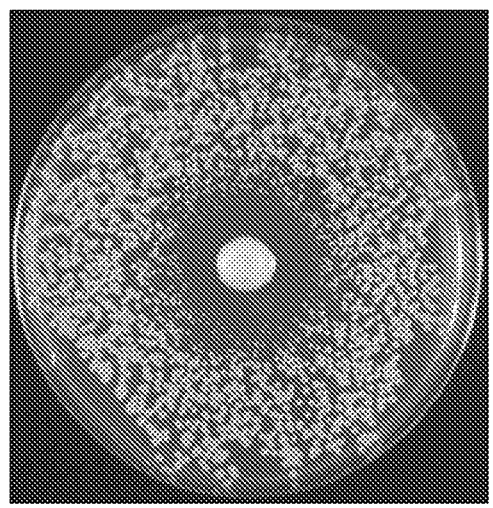
FIGS. 5A and 5B illustrate the comparative antifungal effects of a clotrimazole/activated creatinine composition versus a clotrimazole-only composition, evaluated against yeast *Saccharomyces* spp., as described in Example 5.
Figure 5B:
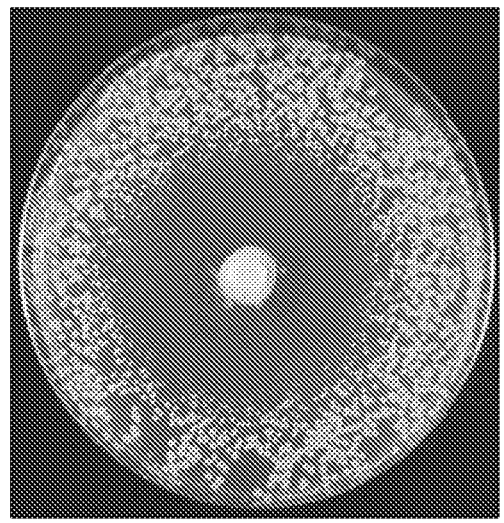

The results are illustrated in FIGS. 5A and 5B. In FIG. 5A, the clotrimazole-only formulation resulted in antifungal activity in the immediate area surrounding the centrally deposited formulation. The clotrimazole-creatinine hydrochloride formulation, as seen in FIG. 5B, resulted in a significantly widened region of antifungal activity.

Example 6—Comparative Antifungal Testing: *Candida albicans*

The procedure of Example 6 was repeated with the same formulation substituting *Candida albicans* for yeast *Saccharomyces* spp.

Figure 6:
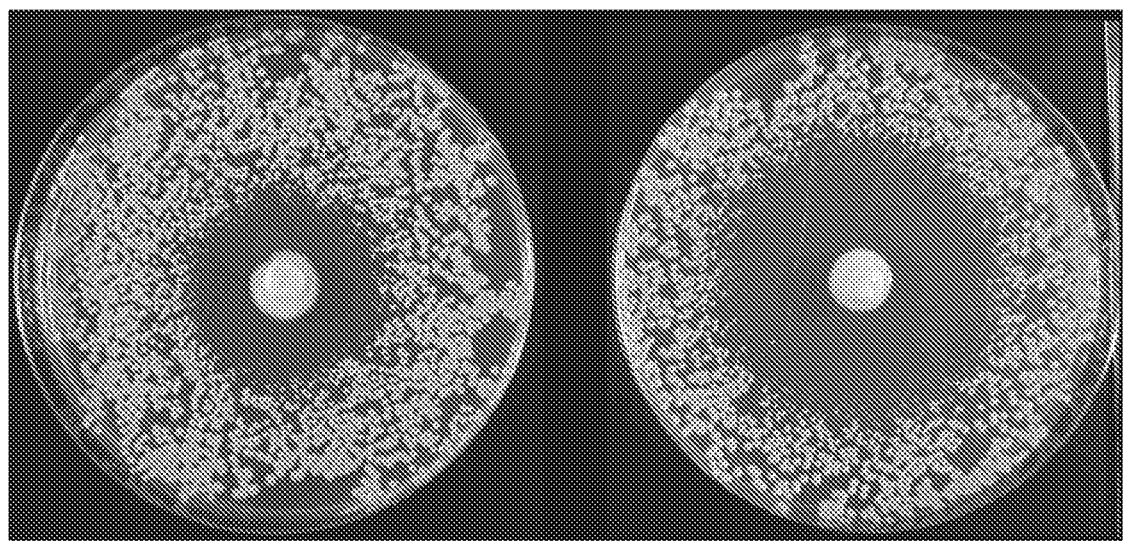
FIG. 6 illustrates the comparative antifungal effects of a clotrimazole/activated creatinine composition versus a clotrimazole-only composition, evaluated against *Candida albicans*, as described in Example 6. On the left is a photograph showing the results obtained with the clotrimazole-only formulation, while on the right is a photograph showing the results obtained with the clotrimazole/activated creatinine composition.

The results are illustrated in FIG. 6, and are analogous to the results obtained in Example 5. That is, in FIG. 6A, the clotrimazole-only formulation resulted in antifungal activity in the immediate area surrounding the centrally deposited formulation. By contrast, the clotrimazole-creatinine hydrochloride formulation, as seen in FIG. 6B, resulted in a significantly widened region of antifungal activity.

Example 7—Comparative Antifungal Testing: *Rhodotorula* Spp

The procedure of Example 5 was repeated with the same formulation substituting *Rhodotorula* spp. for yeast *Saccharomyces* spp.

Figure 7A:
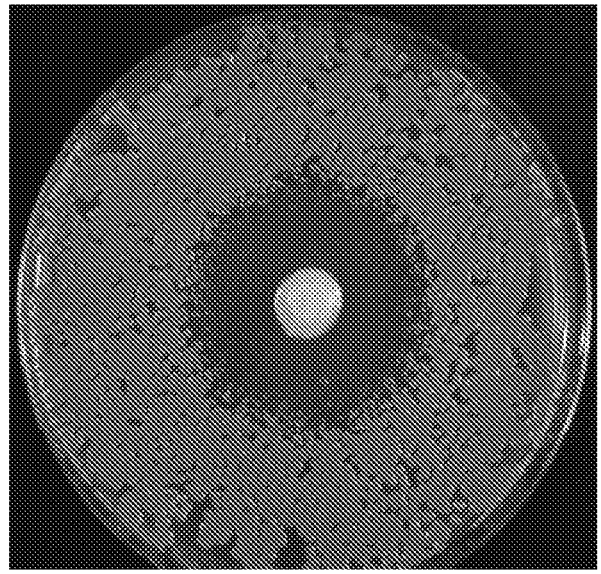
FIGS. 7A and 7B illustrate the comparative antifungal effects of a clotrimazole/activated creatinine composition versus a clotrimazole-only composition, evaluated against *Rhodotorula* spp., as described in Example 7.
Figure 7B:
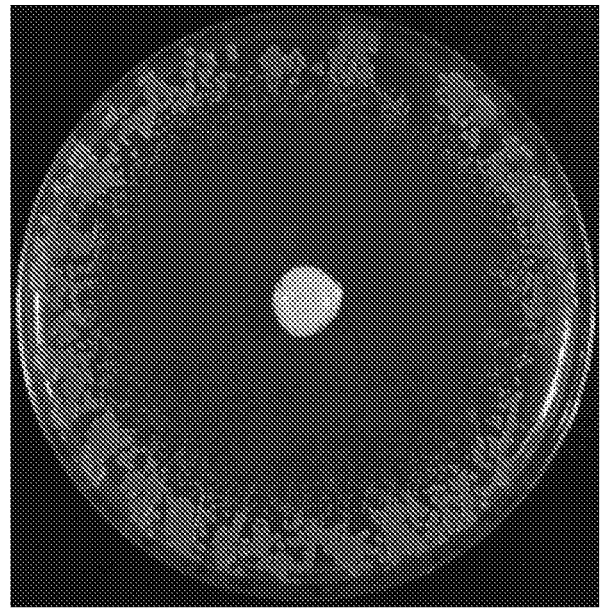

The results are illustrated in FIGS. 7 and 7A, and are analogous to the results obtained in Examples 5 and 6. That is, in FIG. 7A, the clotrimazole-only formulation resulted in antifungal activity in the immediate area surrounding the centrally deposited formulation. By contrast, the clotrimazole/activated creatinine formulation, as seen in FIG. 7B, resulted in a significantly widened region of antifungal activity.

Example 8—Antifungal Testing of Tolnaftate/Activated Creatinine Formulation with *Saccharomyces* Spp.

One gram of commercially available over-the-counter Tinactin® cream containing 1 wt. % of the anti-fungal agent tolnaftate was thoroughly mixed with 2.5 g PEG-400 and 6.5 g water. Creatinine hydrochloride was added to a portion of this 1:10 (0.1%) tolnaftate formulation to yield a 200 mM final concentration; the remaining portion was used as a control. The tolnaftate-creatinine mixture was 30 mM in tolnaftate, giving 13.0 mol % tolnaftate in the tolnaftate-creatinine combination. The tolnaftate/activated creatinine formulation was tested for antifungal activity against *Saccharomyces* spp. by placing approximately 50 microliters onto an LB agar plate that was previously spread with the organism.

The results are illustrated in FIG. 8. As may be seen in the figure, the tolnaftate/activated creatinine formulation did not exhibit any antifungal activity with respect to *Saccharomyces* spp.; the results obtained with the control were virtually identical. It should be noted that in contrast to an imidazole antifungal agent such as clotrimazole, tolnaftate is a polycyclic aromatic compound that does not contain any nitrogen heterocycles, and accordingly is not an azole-type antifungal agent.

Example 9—Antifungal Testing of a Tolnaftate/Activated Creatinine Formulation with *Candida albicans*

The procedure of Example 8 was repeated with the same formulation, but substituting *Candida albicans* for *Saccharomyces* spp.

Figure 9:
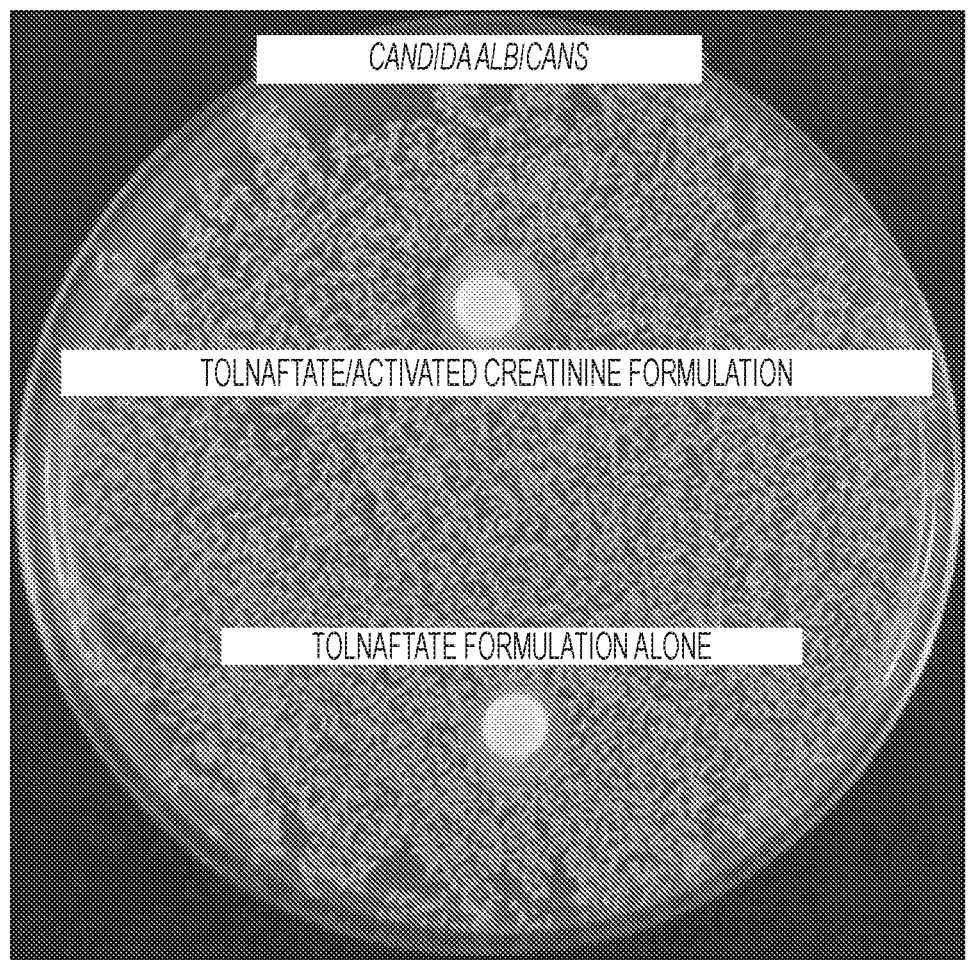
FIG. 9 is a photograph illustrating the antifungal efficacy of a Tinactin® (tolnaftate)/activated creatinine composition against *Candida albicans*, as described in Example 9.

The results are illustrated in FIG. 9. The figure indicates that, as for *Saccharomyces* spp. in the preceding example, the tolnaftate/activated creatinine formulation did not exhibit any antifungal activity with respect to *Candida albicans*.

Example 10—Antimicrobial Testing of Ketoconazole/Activated Creatinine Formulation with Yeast, *S. aureas*, and *E. coli*

A commercial preparation of ketoconazole was obtained (MalAcetic® Ultra Otic cleanser, from Dechra Pharmaceuticals PLC), containing 0.15 wt. % ketoconazole in an acidic solution also containing 1 wt. % hydrocortisone, 2 wt. % boric acid, and 1 wt. % acetic acid. Three formulations were evaluated:

(1) MalAcetic Otic without modification, as a control;

(2) MalAcetic Otic combined with pure CEE to yield a final concentration of 500 mM (7.95 mM ketoconazole at 0.15 wt. % in 500 mM CEE, such that there was 1.6 mol % of ketoconazole in the ketoconazole-creatinine mixture); and (3) Clotrimazole combined with CEE to yield a final concentration of 0.1% w/v clotrimazole and 200 mM CEE in a carrier cream containing 35% w/v erythritol (Eridex 16961 from Cargill, Inc., Cedar Rapids Iowa), 37% w/v propylene glycol, 28% w/v water and 5% w/v dioctyl sulfosuccinate (3.4 mM clotrimazole and 200 mM CEE, such that there was 1.7 mol % clotrimazole in the clotrimazole-creatinine combination).

Data was generated by recording measurements of the zones of inhibition after applying 50 µl of test formulation onto agar plates spread with yeast, *E. coli*, and *S. aureas* (obtained from the same sources as indicated in the preceding examples) and incubating overnight at 37° C.

The test results are shown in FIG. 10, and indicate that the ketoconazole/CEE formulation was superior to the unmodified ketoconazole-only control at killing all three types of organisms, yeast, *E. coli*, and *S. aureas*. Additionally, the results of a comparable clotrimazole/CEE formulation are shown. The positive synergistic properties of this formulation have been shown in the preceding examples. In this example, the zones of inhibition of this clotrimazole/CEE formulation are not as large as those of the ketoconazole/CEE formulation. This illustrates that the degree of potency in a synergistic combination of an imidazole antifungal and activated creatinine can vary with the imidazole agent in the combination, both at the same mol %, as well as with the target microbe.

Example 11—Antifungal and Antimicrobial Testing of a Miconazole/Activated Creatinine Formulation with *Candida albicans* and *S. aureas*

Miconazole cream (2 wt. % miconazole as a miconazole nitrate formulation) was purchased at CVS Pharmacy. Two different formulations of miconazole and activated creatinine were prepared, with the following controls:

(1) A mixture of equal weights of 10 wt. % activated creatinine cream and the 2 wt. % miconazole cream was prepared to give a cream formulation containing 22 mM and 5% activated creatinine, or 350 mM. The amount of miconazole in the miconazole/activated creatinine combination was thus 5.9 mol %.

(2) A mixture of the 2% miconazole cream and the 10 wt. % activated creatinine cream was prepared in a weight ratio of 0.5 to 1.0 miconazole cream to activated creatinine cream. The final formulation contained 30 mM miconazole and 175 mM activated creatinine. The amount of miconazole in the miconazole/activated creatinine combination was thus 14.6 mol %.

(3) Controls: For both (1) and (2), water was substituted for activated creatinine in the formulation.

(4) To determine the effect of activated creatinine alone in the context of a commercially available, over-the-counter antifungal cream, Tinactin®, which has no effect on yeast, was used as a carrier for activated creatinine. Activated creatinine controls were prepared as in (3) but in Tinactin cream.

Figure 11:
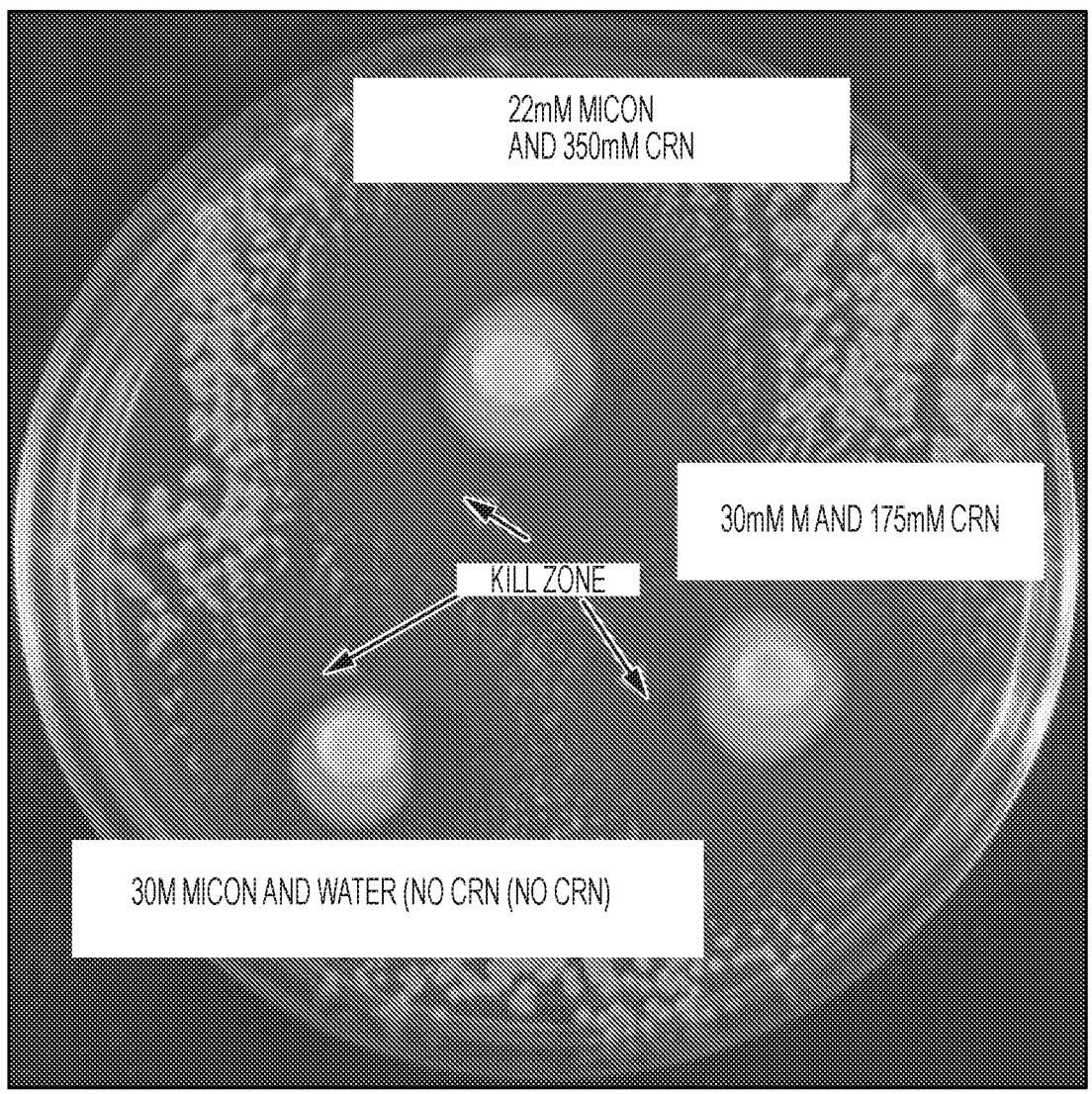
FIG. 11 illustrates the comparable antifungal effects of a miconazole/activated creatinine composition shown in two combination ratios of the components versus a miconazole-only composition, evaluated against *Candida albicans*, as described in Example 11.

The formulations were tested for antifungal activity by placing approximately 50 µl of test formulation onto an LB agar plate spread with *Candida albicans* and *S. aureas* (obtained from the same source indicated in the preceding examples) and incubating overnight at 37° C. Measurements of the zones of inhibition were recorded as in the preceding example. The results are summarized in Table 1, and, for *C. albicans*, illustrated in FIG. 11:

TABLE 1

| Formulation | Zone of Inhibition, mm | |
|---|---|---|
| | C. albicans | S. aureas |
| Miconazole only, 2% | 31 | 0 |
| Miconazole plus activated creatinine, 14.6 mol % miconazole in the combination (30 mM/(30 mM + 175 mM) | 40 | 23 |
| Miconazole plus activated creatinine, 5.9 mol % miconazole in the combination (22 mM/(22 mM + 350 mM) | 44 | 29 |
| Tinactin 30 mM | 0 | 0 |
| Tinactin 21 mM plus 174 mM activated creatinine (10.8 mol % in the combination) | 0 | 13 |
| Tinactin 15 mM plus 350 mM activated creatinine (4.1 mol % in the combination) | 0 | 16 |

The blend of the antifungal agent with the activated creatinine evidences a synergistic increase in both the anti-yeast activity of miconazole and the antibacterial activity of activated creatinine. Consistent with the other tests, in this range of mol % the inhibition increases with a decreased percentage of the imidazole component in the mixture. Tinactin does not exhibit either anti-yeast or antibacterial activity.

Example 12—"Triple Antibiotic" Cream with and without Creatinine Versus a Clotrimazole/Activated Creatinine Combination: Comparison of Antibacterial Activity Against *Pseudomonas*

The following formulations were obtained or prepared and evaluated for antibacterial activity versus *Pseudomonas* bacteria:

(1) A cream containing 15 mM clotrimazole and 500 mM activated creatinine (thus containing 2.9 mol % of clotrimazole in the clotrimazole plus activated creatinine combination).

Figure 12:
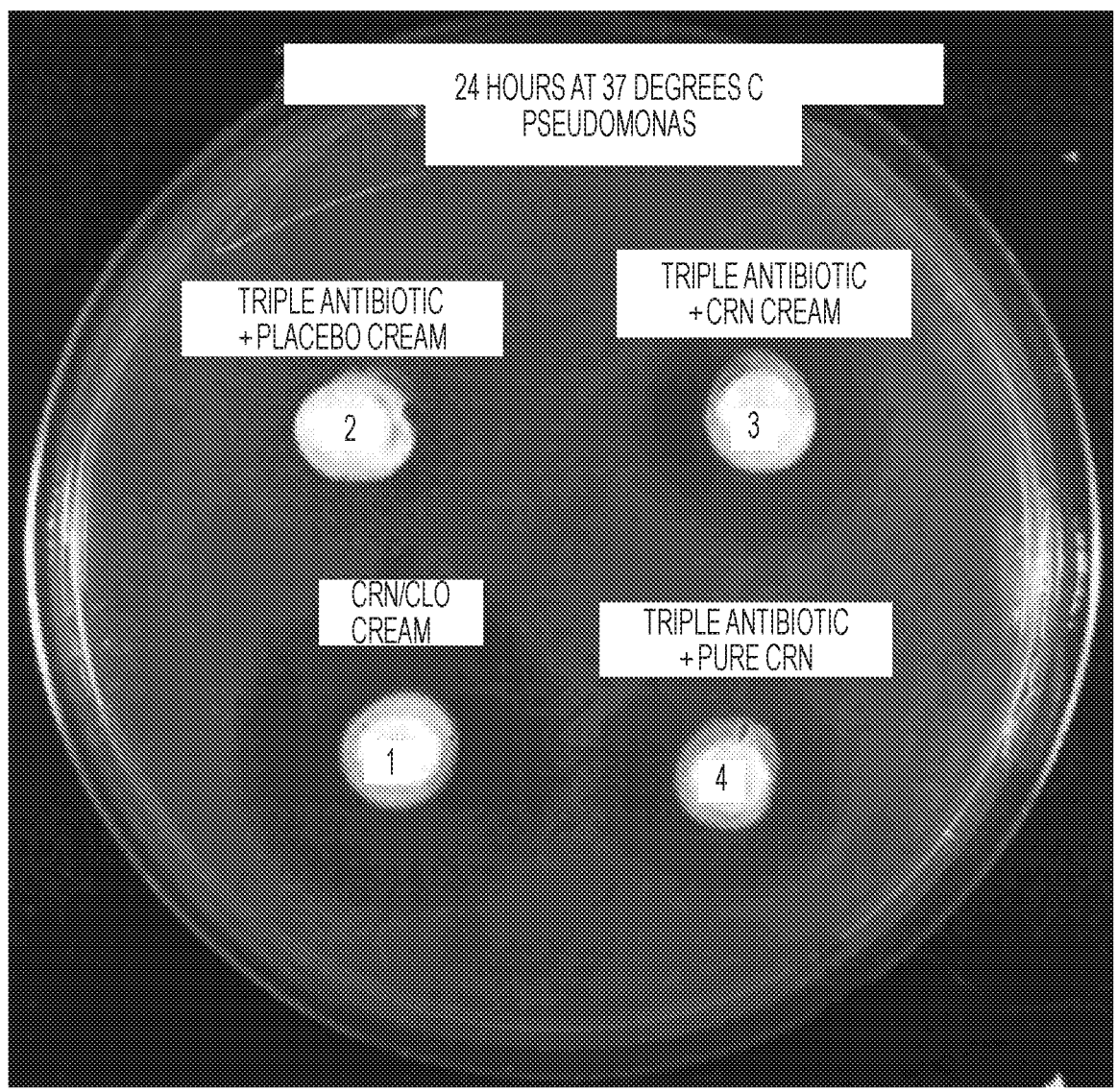
FIGS. 12 and 13 illustrate the comparable antibacterial effects of a clotrimazole/activated creatinine composition versus an over-the-counter triple antibiotic product, evaluated against *Pseudomonas aeruginosa*.

(2) An over-the-counter "triple antibiotic" cream (Bacitracin zinc, USP 500 units; Neomycin, 3.5 mg; Polymyxin B sulfate, USP 10,000 Units; Pramoxine Hydrochloride, USP 10 mg; white petrolatum base), mixed with an equal amount, by weight, of a placebo cream;

(3) The triple antibiotic cream mixed with an equal amount, by weight, of a carrier cream (identical to that used in formulation (3) of Example 10) containing 1.0 M activated clotrimazole;

(4) The triple antibiotic cream mixed with an equal amount, by weight, of the placebo cream, with 1.0 activated creatinine (as creatinine hydrochloride) dissolved into the mixture, to yield a 500 mM concentration. [Data was generated by evaluating the zones of inhibition after applying 50 µl of test formulation onto an LB agar plate spread with *Pseudomonas* (laboratory isolate) and incubating at 37° C. FIG. 12 shows the results after 24 hours and FIG. 13 shows the results after 48 hours.

Figure 13:
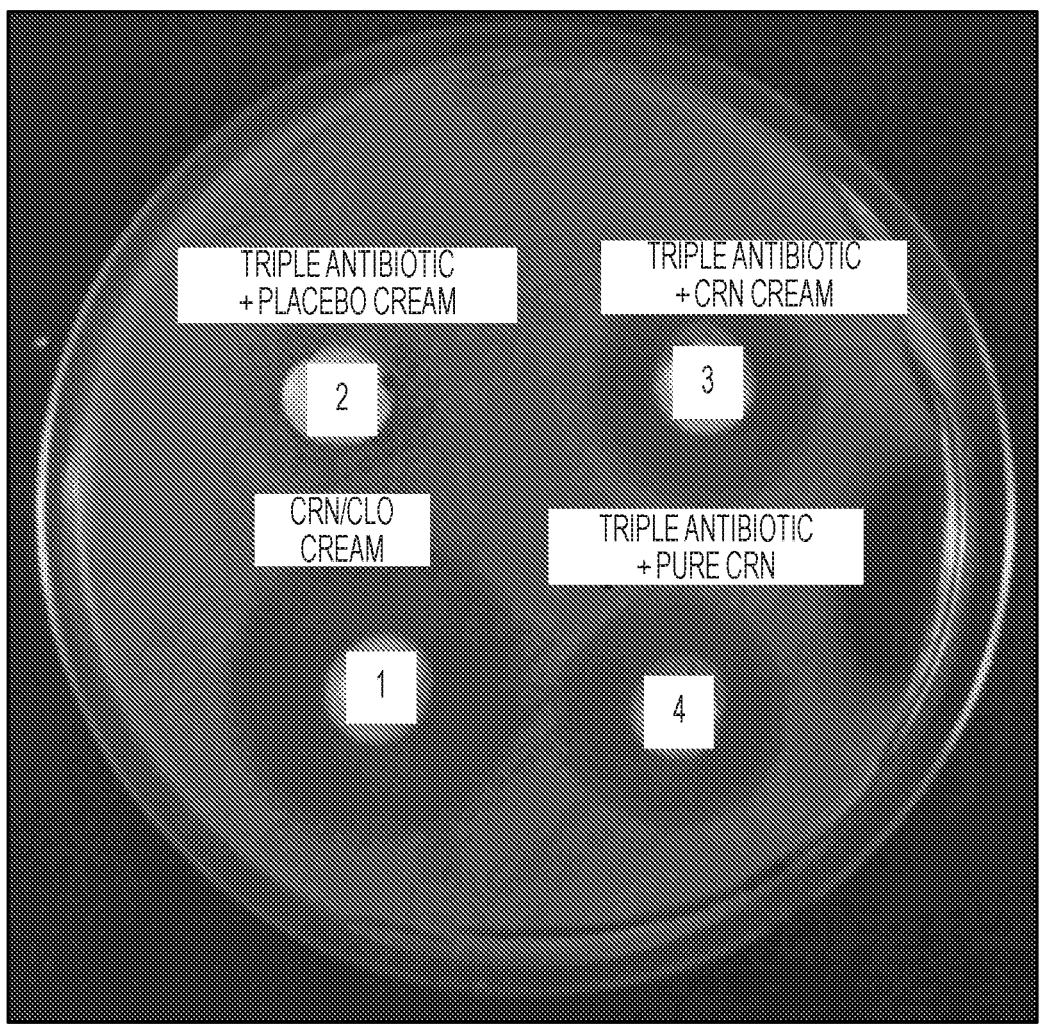

The test results are shown in FIGS. 12 and 13 indicate that the clotrimazole/activated creatinine combination was highly effective against a common but dangerous bacterium, *Pseudomonas aeruginosa*, whereas a standard over-the-counter triple antibiotic product was minimally effective. The figures also show that the over-the-counter product was not synergistic when combined with activated creatinine. The *Pseudomonas aeruginosa* bacterium can be resistant, is highly motile, and can be fatal to patients with weakened immune systems. It is often a problem in hospital settings.

The invention claimed is:

1. An antimicrobial composition comprising a synergistic combination of an imidazole antifungal agent and activated creatinine, wherein the imidazole antifungal agent is in the range of about 0.5 mol % to about 6.5 mol % of the combination of the antifungal agent and the activated creatinine.

2. The antimicrobial composition of claim 1, wherein the imidazole antifungal agent is selected from bifonazole, butoconazole, chlormidazole, clotrimazole, croconazole, econazole, elubiol, fenticonazole, flutrimazole, isoconazole, ketoconazole, luliconazole, miconazole, neticonazole, omoconazole, oxiconazole, sertaconazole, sulconazole, tiaconazole, and combinations thereof.

3. The antimicrobial composition of claim 2, wherein the imidazole antifungal agent is selected from clotrimazole, ketoconazole, and miconazole.

4. The antimicrobial composition of claim 1, wherein the imidazole antifungal agent comprises clotrimazole.

5. The antimicrobial composition of claim 1, further including a pharmaceutically acceptable carrier.

6. The antimicrobial composition of claim 5, wherein the pharmaceutically acceptable carrier is suitable as a carrier for topical administration.

7. The antimicrobial composition of claim 5, wherein the pharmaceutically acceptable carrier is suitable as a carrier for systemic administration.

8. The antimicrobial composition of claim 1, further including an additional pharmacologically active agent.

9. The antimicrobial composition of claim 1, further including at least one excipient selected from penetration enhancers, stabilizers, emulsifiers, thickening agents, film-forming agents, skin protectants, pH adjusting agents, diluents, emollients, preservatives, and combinations thereof.

10. A method for increasing the antibacterial efficacy of activated creatinine, wherein the method comprises combining the activated creatinine with an imidazole antifungal agent in a composition in which the imidazole antifungal agent is in the range of about 0.5 mol % to about 6.5 mol % of the combination of the antifungal agent and the activated creatinine, such that the antibacterial efficacy of the composition is greater than the antibacterial efficacy of activated creatinine alone.

11. A method for increasing the antifungal efficacy of an imidazole antifungal agent, wherein the method comprises combining the imidazole antifungal agent with activated creatinine in a composition in which the imidazole antifungal agent is in the range of about 0.5 mol % to about 6.5 mol % of the combination of the antifungal agent and the activated creatinine, such that the antifungal efficacy of the composition is greater than the antifungal efficacy of the imidazole antifungal agent alone.

12. The antimicrobial composition of claim 1, wherein the activated creatinine is creatinine hydrochloride.

13. The antimicrobial composition of claim 3, wherein the activated creatinine is creatinine hydrochloride.

14. The method of claim 10, wherein the activated creatinine is creatinine hydrochloride.

15. The method of claim 10, wherein the imidazole antifungal agent is selected from bifonazole, butoconazole, chlormidazole, clotrimazole, croconazole, econazole, elubiol, fenticonazole, flutrimazole, isoconazole, ketoconazole, luliconazole, miconazole, neticonazole, omoconazole, oxiconazole, sertaconazole, sulconazole, tiaconazole, and combinations thereof.

16. The method of claim 15, wherein the imidazole antifungal agent is selected from clotrimazole, ketoconazole, and miconazole.

17. The method of claim 16, wherein the activated creatinine is creatinine hydrochloride.

18. The method of claim 11, wherein the activated creatinine is creatinine hydrochloride.

19. The method of claim 11, wherein the imidazole antifungal agent is selected from bifonazole, butoconazole, chlormidazole, clotrimazole, croconazole, econazole, elubiol, fenticonazole, flutrimazole, isoconazole, ketoconazole, luliconazole, miconazole, neticonazole, omoconazole, oxiconazole, sertaconazole, sulconazole, tiaconazole, and combinations thereof.

20. The method of claim 19, wherein the imidazole antifungal agent is selected from clotrimazole, ketoconazole, and miconazole.

21. The method of claim 20, wherein the activated creatinine is creatinine hydrochloride.

* * * * *